(12) United States Patent
Feinberg

(10) Patent No.: US 9,790,552 B2
(45) Date of Patent: Oct. 17, 2017

(54) DETECTION OF ORGAN REJECTION

(71) Applicant: THE BRIGHAM AND WOMEN'S HOSPITAL, INC., Boston, MA (US)

(72) Inventor: Mark W. Feinberg, Newton, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 14/788,843

(22) Filed: Jul. 1, 2015

(65) Prior Publication Data

US 2016/0010156 A1    Jan. 14, 2016

Related U.S. Application Data

(63) Continuation of application No. 12/520,426, filed as application No. PCT/US2007/026091 on Dec. 20, 2007, now abandoned.

(60) Provisional application No. 60/876,076, filed on Dec. 20, 2006.

(51) Int. Cl.
*C12Q 1/68* (2006.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 6,582,908 | B2 | 6/2003 | Fodor et al. | |
|---|---|---|---|---|
| 2004/0157790 | A1 | 8/2004 | Herweijer et al. | |
| 2005/0059005 | A1 | 3/2005 | Tuschl et al. | |
| 2006/0105360 | A1 | 5/2006 | Croce et al. | |
| 2007/0238094 | A1 | 10/2007 | Chaussabel et al. | |
| 2008/0171667 | A1 | 7/2008 | Brown et al. | |
| 2008/0306018 | A1* | 12/2008 | Croce .................. | C12Q 1/6886 514/44 A |
| 2009/0123912 | A1 | 5/2009 | Raymond | |

FOREIGN PATENT DOCUMENTS

WO    2006014625 A1    2/2006

OTHER PUBLICATIONS

Sempere, et al. (2004) Genome Biology, V.5:R13.*
Alvarez-Garcia et al., "MicroRNA functions in animal development and human disease", Development (2005). 132:4653-4662.
Calin et al., "A Micro-RNA Signature Associated with Prognosis and Progression in Chronic Lymphocytic Leukemia", N. Engl. J. Med. 353(17):1793-1801 (2005).
Deng et al., "Noninvasive Discrimination of Rejection in Cardiac Allograft Recipients Using Gene Expression Profiling", Am. J. Transplant. 6:150-160 (2006).
Evans et al., "The Economic Implications of Noninvasive Molecular Testing for Cardiac Allograft Rejection", Am. J. Transplant. 5:1553-1558 (2005).
Febbo et al., "Application of Oligonucleotide Microarrays to Assess the Biological Effects of Neoadjuvant Imatinib Mesylate Treatment for Localized Prostate Cancer", Clin. Cancer Res. 12(1):152-158 (2006).
Lu et al., "MicroRNA expression profiles classify human cancers", Nature 435(9):834-838 (2005).
Miska et al., "Microarray analysis of microRNA expression in the developing mammalian brain", Genome Biology 5: R68.1-R68.13 (2004).
Shingara et al., "An optimized isolation and labeling platform for accurate microRNA expression profiling" RNA 11 (9):1461-1470 (2005).
Volinia et al., "A microRNA expression signature of human solid tumors defines cancer gene targets", PNAS 103 (7):2257-2261 (2006).
WO-PCT/ISA/237—Written Opinion issued in PCT/US07/26901 (2008).
WO-PCT/ISA/210—ISR issued in PCT/US07/26091 (2008).

* cited by examiner

*Primary Examiner* — Jennifer McDonald
(74) *Attorney, Agent, or Firm* — Nixon Peabody LLP; Mark J. FitzGerald; Teresa A. Ptashka

(57) ABSTRACT

The present invention features methods and compositions for the non-invasive detection of organ rejection using a microRNA score.

12 Claims, 2 Drawing Sheets

DETECTION OF ORGAN REJECTION

CROSS-REFERENCE TO RELATED APPLICATIONS

This application is a Continuation of U.S. patent application Ser. No. 12/520,426 filed on Nov. 23, 2009, which is a 371 National Phase Entry of International Patent Application No. PCT/US207/026091 filed on Dec. 20, 2007 which claims benefit under 35 U.S.C. §119(e) of U.S. Provisional Patent Application Ser. No. 60/876,076 filed on Dec. 20, 2006, the contents of which are incorporated herein by reference in their entirety.

STATEMENT OF RIGHTS TO INVENTIONS MADE UNDER FEDERALLY SPONSORED RESEARCH

This invention was made with Government support under Grant Nos. CA057341, CA051497 and HL 080174 awarded by the Public Health Services/National Institutes of Health. The Government has certain rights in this invention

BACKGROUND OF THE INVENTION

Each day, about 74 people are recipients of organ transplants. Depending on the transplanted organ, many, if not all patients experience an episode of immunorejection. Biopsy of the transplanted organ is one method to confirm rejection; however this invasive approach makes it suboptimal for many patients for a variety of reasons, including patient discomfort, inconvenience, low but definite risks of morbidity and death, and increased health care costs. Biopsy procedures often suffer from sampling errors and variable, subjective pathological interpretation. In addition, there is emerging evidence that a transplanted organ may show a 'clinical rejection' despite a 'normal' pathologic specimen, suggesting a dysregulation that occurs at the molecular level preceding the onset of cellular rejection. Thus, non-invasive monitoring of transplant rejection would provide a less costly, and more convenient method of monitoring transplant rejection in patients. Further, non-invasive monitoring of transplant rejection would provide an earlier means for detecting transplant rejection. However, no alternative to the invasive biopsy procedure currently exists. Accordingly, improved methods and compositions for the non-invasive detection of organ rejection are needed.

SUMMARY OF THE INVENTION

The invention is based, at least in part, on the discovery that MicroRNAs can be used for the non-invasive detection of organ rejection. MicroRNAs (miRNAs) are a recently discovered class of small, evolutionary conserved non-coding RNA species that have diverse biological functions, including the ability to regulate key genes involved in cellular activation and stress response. miRNAs are typically about 17-23 nucleotides in length, and regulate the stability or translational efficiency of target mRNAs.

The present invention features methods and compositions for the non-invasive detection of organ rejection using a microRNA score. Thus, in one aspect, the invention provides a method for identifying a subject as having, or having a propensity to develop, organ rejection, the method comprising: measuring the amount of small non-coding RNA expression in a biological sample from the subject and detecting an altered amount of expression relative to a reference, thereby identifying a subject as having, or having a propensity to develop, organ rejection. In one embodiment, the organ rejection occurs after transplantation of the organ into the subject.

Another aspect of the invention provides a method for monitoring a transplant recipient at risk for organ rejection, the method comprising determining the amount of small non-coding RNA expression in a biological sample obtained from the recipient, wherein an altered amount of expression relative to a reference indicates that the recipient has, or has a propensity to develop, organ rejection.

According to the invention, the small non-coding RNA can be microRNA. Other examples of small non-coding RNA include transfer RNA (tRNA), ribosomal RNA (rRNA), small nuclear RNA (snRNA), small nucleolar RNA (snoRNA), or signal recognition particle RNA complex (SRP). In a specific embodiment, the small non-coding RNA is selected from the group consisting of:

```
mmu-miR134,
                              (SEQ ID NO: 1)
UGUGACUGGUUGACCAGAGGGG, mmu-miR144,
                              (SEQ ID NO: 2)
UACAGUAUAGAUGAUGUACUAG, mmu-miR466,
                              (SEQ ID NO: 3)
AUACAUACACGCACACAUAAGAC, mmu-miR7,
                              (SEQ ID NO: 4)
UGGAAGACUAGUGAUUUUGUUG, mmu-miR346,
                              (SEQ ID NO: 5)
UGUCUGCCCGAGUGCCUGCCUCU, mmu-miR468,
                              (SEQ ID NO: 6)
UAUGACUGAUGUGCGUGUGUCU, mmu-miR188,
                              (SEQ ID NO: 7)
CAUCCCUUGCAUGGUGGAGGGU, mmu-miR298,
                              (SEQ ID NO: 8)
GGCAGAGGAGGGCUGUUCUUCC, mmu-miR-467,
                              (SEQ ID NO: 9)
AUAUACAUACACACACCUACAC, mmu-miR-292-5p,
                              (SEQ ID NO: 10)
ACUCAAACUGGGGGCUCUUUUG, mmu-miR-186,
                              (SEQ ID NO: 11)
CAAAGAAUUCUCCUUUUGGGCUU, mmu-miR-486,
                              (SEQ ID NO: 12)
UCCUGUACUGAGCUGCCCCGAG, mmu-miR-451,
                              (SEQ ID NO: 13)
AAACCGUUACCAUUACUGAGUU, mmu-miR-18,
                              (SEQ ID NO: 14)
UAAGGUGCAUCUAGUGCAGAUA,
```

-continued mmu-miR-25,
(SEQ ID NO: 15)
CAUUGCACUUGUCUCGGUCUGA, mmu-miR-223
(SEQ ID NO: 16)
UGUCAGUUUGUCAAAUACCCC, mmu-miR-320,
(SEQ ID NO: 17)
AAAAGCUGGGUUGAGAGGGCGAA, mmu-miR-148b,
(SEQ ID NO: 18)
UCAGUGCAUCACAGAACUUUGU, mmu-miR-21,
(SEQ ID NO: 19)
UAGCUUAUCAGACUGAUGUUGA, mmu-miR-124a,
(SEQ ID NO: 20)
UAAGGCACGCGGUGAAUGCC, mmu-miR-19a,
(SEQ ID NO: 21)
UGUGCAAAUCUAUGCAAAACUGA, mmu-miR-301
(SEQ ID NO: 22)
CAGUGCAAUAGUAUUGUCAAAGC, mmu-miR-31,
(SEQ ID NO: 23)
AGGCAAGAUGCUGGCAUAGCUG, mmu-miR-20,
(SEQ ID NO: 24)
UAAAGUGCUUAUAGUGCAGGUAG, mmu-miR-29c,
(SEQ ID NO: 25)
UAGCACCAUUUGAAAUCGGU, mmu-miR-148a,
(SEQ ID NO: 26)
UCAGUGCACUACAGAACUUUGU, mmu-miR-17-5p,
(SEQ ID NO: 27)
CAAAGUGCUUACAGUGCAGGUAGU, mmu-miR-185,
(SEQ ID NO: 28)
UGGAGAGAAAGGCAGUUC, mmu-miR-106a,
(SEQ ID NO: 29)
CAAAGUGCUAACAGUGCAGGUA, mmu-miR-106b,
(SEQ ID NO: 30)
UAAAGUGCUGACAGUGCAGAU, mmu-miR375,
(SEQ ID NO: 31)
UUUGUUCGUUCGGCUCGCGUGA, mmu-miR216,
(SEQ ID NO: 32)
UAAUCUCAGCUGGCAACUGUG, mmu-miR217,
(SEQ ID NO: 33)
UACUGCAUCAGGAACUGACUGGAU, mmu-miR200a,
(SEQ ID NO: 34)
UAACACUGUCUGGUAACGAUGU, mmu-miR200b,
(SEQ ID NO: 35)
UAAUACUGCCUGGUAAUGAUGAC, mmu-miR429,
(SEQ ID NO: 36)
UAAUACUGUCUGGUAAUGCCGU, mmu-miR200c,
(SEQ ID NO: 37)
UAAUACUGCCGGGUAAUGAUGG, mmu-miR141
(SEQ ID NO: 38)
UAACACUGUCUGGUAAAGAUGG, mmu-miR148a,
(SEQ ID NO: 39)
UCAGUGCACUACAGAACUUUGU, mmu-miR152,
(SEQ ID NO: 40)
UCAGUGCAUGACAGAACUUGGG, mmu-miR182,
(SEQ ID NO: 41)
UUUGGCAAUGGUAGAACUCACA, mmu-miR99a,
(SEQ ID NO: 42)
ACCCGUAGAUCCGAUCUUGU, mmu-miR-130a,
(SEQ ID NO: 43)
CAGUGCAAUGUUAAAAGGGCAU, mmu-miR-127,
(SEQ ID NO: 44)
UCGGAUCCGUCUGAGCUUGGC, mmu-miR-100,
(SEQ ID NO: 45)
AACCCGUAGAUCCGAACUUGUG, mmu-miR-199a,
(SEQ ID NO: 46)
CCCAGUGUUCAGACUACCUGUUC, mmu-miR-199b,
(SEQ ID NO: 47)
CCCAGUGUUUAGACUACCUGUUC, mmu-miR-125a,
(SEQ ID NO: 48)
UCCCUGAGACCCUUUAACCUGUG, mmu-miR-22,
(SEQ ID NO: 49)
AAGCUGCCAGUUGAAGAACUGU, mmu-miR-434-3p,
(SEQ ID NO: 50)
UUUGAACCAUCACUCGACUCC, mmu-miR-34a,
(SEQ ID NO: 51)
UGGCAGUGUCUUAGCUGGUUGUU, mmu-miR-181c,
(SEQ ID NO: 52)
AACAUUCAACCUGUCGGUGAGU, mmu-miR-139,
(SEQ ID NO: 53)
UCUACAGUGCACGUGUCU, mmu-miR-130a,
(SEQ ID NO: 54)
CAGUGCAAUGUUAAAAGGGCAU, -continued mmu-miR-322,
(SEQ ID NO: 55)
CAGCAGCAAUUCAUGUUUUGGA, mmu-miR-181a,
(SEQ ID NO: 56)
AACAUUCAACGCUGUCGGUGAGU, mmu-miR-125a,
(SEQ ID NO: 57)
UCCCUGAGACCCUUUAACCUGUG, mmu-miR-200b,
(SEQ ID NO: 58)
UAAUACUGCCUGGUAAUGAUGAC, mmu-miR-145,
(SEQ ID NO: 59)
GUCCAGUUUUCCCAGGAAUCCCUU, mmu-miR-127,
(SEQ ID NO: 60)
UCGGAUCCGUCUGAGCUUGGC, mmu-miR-199a,
(SEQ ID NO: 61)
CCCAGUGUUCAGACUACCUGUUC, mmu-miR-425,
(SEQ ID NO: 62)
AUCGGGAAUGUCGUGUCCGCC, mmu-miR-99b,
(SEQ ID NO: 63)
CACCCGUAGAACCGACCUUGCG, mmu-let-7e,
(SEQ ID NO: 64)
UGAGGUAGGAGGUUGUAUAGU, mmu-miR-195,
(SEQ ID NO: 65)
UAGCAGCACAGAAAUAUUGGC, mmu-miR-152,
(SEQ ID NO: 66)
UCAGUGCAUGACAGAACUUGGG, mmu-miR-125b,
(SEQ ID NO: 67)
UCCCUGAGACCCUAACUUGUGA, mmu-miR-187,
(SEQ ID NO: 68)
UCGUGUCUUGUGUUGCAGCCGG mmu-miR-324-3p,
(SEQ ID NO: 69)
CCACUGCCCCAGGUGCUGCUGG, mmu-miR-150,
(SEQ ID NO: 70)
UCUCCCAACCCUUGUACCAGUG, mmu-miR-28,
(SEQ ID NO: 71)
AAGGAGCUCACAGUCUAUUGAG,
and mmu-miR-143
(SEQ ID NO: 72)
UGAGAUGAAGCACUGUAGCUCA, and also includes combinations thereof.

In various embodiments, the organ is heart, kidney, liver, lung, or pancreas. In a specific embodiment, the organ is a heart.

In a further embodiment, the amount of small non-coding RNA expression is determined using a microarray. In one embodiment, the microarray comprises a chip, plate, bead, or membrane. In another embodiment, the biological sample comprises blood cells, biopsy specimens, urine cells/urine sediment, or cells found in sputum. In a specific embodiment, the blood cells are peripheral blood mononuclear cells. In still a further specific embodiment, the blood cells are leukocytes. In another embodiment, the biopsy specimens are endomyocardial biopsy specimens or biopsy specimens from kidney, lung, liver, or pancreas.

Any of the methods of the invention can be used to determine the efficacy of, or monitor, a treatment regimen for a subject having organ rejection. In a further embodiment, methods of the invention are used to determine the prognosis of a subject having organ rejection. In a particular embodiment, the prognosis determines the treatment regimen for the subject.

In another embodiment, the invention further provides obtaining the small non-coding RNAs.

In yet another aspect, the invention provides a diagnostic kit for the diagnosis of a subject having, or having a propensity to develop, organ rejection, comprising at least one nucleic acid molecule complementary to a small non-coding RNA, and written instructions for use of the kit for the diagnosis of the subject having, or having a propensity to develop, organ rejection. The kit can further comprise an adsorbent, wherein the adsorbent retains at least one small non-coding RNA molecule.

In another aspect, the invention provides a method for obtaining an organ rejection score, the method comprising collecting a sample of RNA from subjects undergoing organ rejection, isolating and purifying microRNA from the sample, labeling the microRNAs with a signal emitting agent, hybridizing the microRNAs to substrates containing oligonucleotides that are complementary to the microRNAs, detecting the signal for each hybridized microRNA, calculating an average value between the detected signals and a reference signal and obtaining a ratio of the signal between the sample and the reference, thereby obtaining an organ rejection score.

In yet another aspect, the invention provides a diagnostic kit for obtaining an organ rejection score comprising a substrate for hybridizing labeled, microRNAs of the invention to complementary oligonucleotides and instructions for detecting the signal for each hybridized microRNA, calculating an average value between the detected signals and a reference signal and obtaining a ratio of the signal between the sample and the reference.

In yet another aspect, the invention provides an identified RNA profile indicating organ rejection comprised of any one or more of SEQ ID NO: 1-SEQ ID NO: 72, and combinations thereof.

In one embodiment, the invention provides an identified RNA profile indicating organ rejection comprising an increased amount of one or more small non-coding RNAs selected from the group consisting of:

mmu-miR134,
(SEQ ID NO: 1)
UGUGACUGGUUGACCAGAGGGG, mmu-miR144,
(SEQ ID NO: 2)
UACAGUAUAGAUGAUGUACUAG, mmu-miR466,
(SEQ ID NO: 3)
AUACAUACACGCACACAUAAGAC, mmu-miR7,
(SEQ ID NO: 4)
UGGAAGACUAGUGAUUUUGUUG, mmu-miR346,
(SEQ ID NO: 5)
UGUCUGCCCGAGUGCCUGCCUCU, mmu-miR468,
(SEQ ID NO: 6)
UAUGACUGAUGUGCGUGUGUCU, mmu-miR188,
(SEQ ID NO: 7)
CAUCCCUUGCAUGGUGGAGGGU, mmu-miR298,
(SEQ ID NO: 8)
GGCAGAGGAGGGCUGUUCUUCC, mmu-miR-467,
(SEQ ID NO: 9)
AUAUACAUACACACACCUACAC, mmu-miR-292-5p,
(SEQ ID NO: 10)
ACUCAAACUGGGGGCUCUUUUG, mmu-miR-186,
(SEQ ID NO: 11)
CAAAGAAUUCUCCUUUUGGGCUU, mmu-miR-486,
(SEQ ID NO: 12)
UCCUGUACUGAGCUGCCCCGAG, mmu-miR-451,
(SEQ ID NO: 13)
AAACCGUUACCAUUACUGAGUU, mmu-miR-18,
(SEQ ID NO: 14)
UAAGGUGCAUCUAGUGCAGAUA, mmu-miR-25,
(SEQ ID NO: 15)
CAUUGCACUUGUCUCGGUCGA, mmu-miR-223
(SEQ ID NO: 16)
UGUCAGUUUGUCAAAUACCCC, mmu-miR-320,
(SEQ ID NO: 17)
AAAAGCUGGGUUGAGAGGGCGAA, mmu-miR-148b,
(SEQ ID NO: 18)
UCAGUGCAUCACAGAACUUUGU, mmu-miR-21,
(SEQ ID NO: 19)
UAGCUUAUCAGACUGAUGUUGA, mmu-miR-124a,
(SEQ ID NO: 20)
UAAGGCACGCGGUGAAUGCC, mmu-miR-19a,
(SEQ ID NO: 21)
UGUGCAAAUCUAUGCAAAACUGA, mmu-miR-301
(SEQ ID NO: 22)
CAGUGCAAUAGUAUUGUCAAAGC, mmu-miR-31,
(SEQ ID NO: 23)
AGGCAAGAUGCUGGCAUAGCUG, mmu-miR-20,
(SEQ ID NO: 24)
UAAAGUGCUUAUAGUGCAGGUAG, mmu-miR-29c,
(SEQ ID NO: 25)
UAGCACCAUUUGAAAUCGGU, mmu-miR-148a,
(SEQ ID NO: 26)
UCAGUGCACUACAGAACUUUGU, mmu-miR-17-5p,
(SEQ ID NO: 27)
CAAAGUGCUUACAGUGCAGGUAGU, mmu-miR-185,
(SEQ ID NO: 28)
UGGAGAGAAAGGCAGUUC, mmu-miR-106a,
(SEQ ID NO: 29)
CAAAGUGCUAACAGUGCAGGUA,
and mmu-miR-106b,
(SEQ ID NO: 30)
UAAAGUGCUGACAGUGCAGAU, and also includes combinations thereof.

In another embodiment, the invention provides an identified RNA profile indicating organ rejection comprising a decreased amount of small non-coding RNA selected from the group consisting of:

mmu-miR375,
(SEQ ID NO: 31)
UUUGLTUCGUUCGGCUCGCGUGA, mmu-miR216,
(SEQ ID NO: 32)
UAAUCUCAGCUGGCAACUGUG, mmu-miR217,
(SEQ ID NO: 33)
UACUGCAUCAGGAACUGACUGGAU, mmu-miR200a,
(SEQ ID NO: 34)
UAACACUGUCUGGUAACGAUGU, mmu-miR200b,
(SEQ ID NO: 35)
UAAUACUGCCUGGUAAUGAUGAC, mmu-miR429,
(SEQ ID NO: 36)
UAAUACUGUCUGGUAAUGCCGU, mmu-miR200c,
(SEQ ID NO: 37)
UAAUACUGCCGGGUAAUGAUGG, mmu-miR141
(SEQ ID NO: 38)
UAACACUGUCUGGUAAAGAUGG, mmu-miR148a,
(SEQ ID NO: 39)
UCAGUGCACUACAGAACUUUGU, mmu-miR152,
(SEQ ID NO: 40)
UCAGUGCAUGACAGAACUUGGG, mmu-miR182,
(SEQ ID NO: 41)
UUUGGCAAUGGUAGAACUCACA, -continued mmu-miR99a,
ACCCGUAGAUCCGAUCUUGU, (SEQ ID NO: 42)

mmu-miR-130a,
CAGUGCAAUGUUAAAAGGGCAU, (SEQ ID NO: 43)

mmu-miR-127,
UCGGAUCCGUCUGAGCUUGGC, (SEQ ID NO: 44)

mmu-miR-100,
AACCCGUAGAUCCGAACUUGUG, (SEQ ID NO: 45)

mmu-miR-199a,
CCCAGUGUUCAGACUACCUGUUC, (SEQ ID NO: 46)

mmu-miR-199b,
CCCAGUGUUUAGACUACCUGUUC, (SEQ ID NO: 47)

mmu-miR-125a,
UCCCUGAGACCCUUUAACCUGUG, (SEQ ID NO: 48)

mmu-miR-22,
AAGCUGCCAGUUGAAGAACUGU, (SEQ ID NO: 49)

mmu-miR-434-3p,
UUUGAACCAUCACUCGACUCC, (SEQ ID NO: 50)

mmu-miR-34a,
UGGCAGUGUCUUAGCUGGUUGUU, (SEQ ID NO: 51)

mmu-miR-181c,
AACAUUCAACCUGUCGGUGAGU, (SEQ ID NO: 52)

mmu-miR-139,
UCUACAGUGCACGUGUCU, (SEQ ID NO: 53)

mmu-miR-130a,
CAGUGCAAUGUIJAAAAGGGCAU, (SEQ ID NO: 54)

mmu-miR-322,
CAGCAGCAAUUCAUGUUUUGGA, (SEQ ID NO: 55)

mmu-miR-181a,
AACAUUCAACGCUGUCGGUGAGU, (SEQ ID NO: 56)

mmu-miR-125a,
UCCCUGAGACCCUUUAACCUGUG, (SEQ ID NO: 57)

mmu-miR-200b,
UAAUACUGCCUGGUAAUGAUGAC, (SEQ ID NO: 58)

mmu-miR-145,
GUCCAGUUUUCCCAGGAAUCCCUU, (SEQ ID NO: 59)

mmu-miR-127,
UCGGAUCCGUCUGAGCUUGGC, (SEQ ID NO: 60)

mmu-miR-199a,
CCCAGUGUUCAGACUACCUGUUC, (SEQ ID NO: 61)

mmu-miR-425,
AUCGGGAAUGUCGUGUCCGCC, (SEQ ID NO: 62)

mmu-miR-99b,
CACCCGUAGAACCGACCUUGCG, (SEQ ID NO: 63)

mmu-let-7e,
UGAGGUAGGAGGUUGUAUAGU, (SEQ ID NO: 64)

mmu-miR-195,
UAGCAGCACAGAAAUAUUGGC, (SEQ ID NO: 65)

mmu-miR-152,
UCAGUGCAUGACAGAACUUGGG, (SEQ ID NO: 66)

mmu-miR-125b,
UCCCUGAGACCCUAACUUGUGA, (SEQ ID NO: 67)

mmu-miR-187,
UCGUGUCUUGUGUUGCAGCCGG, (SEQ ID NO: 68)

mmu-miR-324-3p,
CCACUGCCCCAGGUGCUGCUGG, (SEQ ID NO: 69)

mmu-miR-150,
UCUCCCAACCCUUGUACCAGUG, (SEQ ID NO: 70)

mmu-miR-28,
AAGGAGCUCACAGUCUAUUGAG, (SEQ ID NO: 71)
and mmu-miR-143
UGAGAUGAAGCACUGUAGCUCA, (SEQ ID NO: 72)

and includes combinations thereof.

Profiles of the invention can be stored by electronic means.

DETAILED DESCRIPTION OF THE INVENTION

Figure 1A:
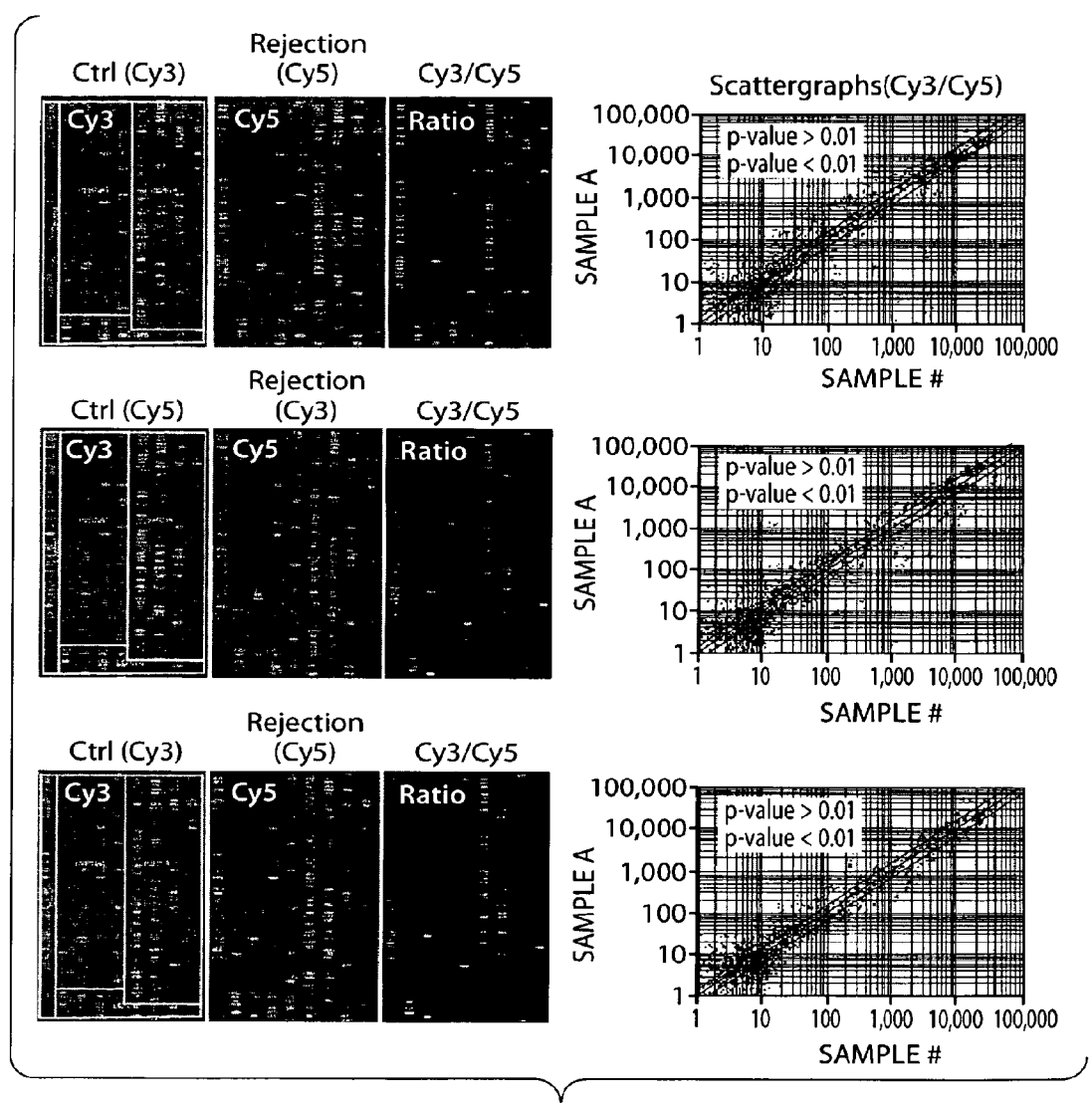
FIG. 1A shows fluorescent hybridization of microRNA samples (Cy3 or Cy5 labeled) to mouse microRNA chips containing 464 oligonucleotides for mature or pre-microRNAs.

The present invention is based in part on the discovery that several microRNAs are altered (e.g., increased or decreased) in response to organ failure (e.g., acute cardiac rejection). Accordingly, the invention provides methods and compositions for the non-invasive detection of organ rejection using a microRNA score.

1. Definitions

Unless defined otherwise, all technical and scientific terms used herein have the meaning commonly understood by a person skilled in the art to which this invention belongs. As used herein, the following terms have the meanings ascribed to them below, unless specified otherwise.

The term "subject" is intended to include vertebrates, preferably a mammal. Mammals include, but are not limited to, humans.

The term "organ rejection" refers to the failure of a transplanted organ in a subject resulting from an adverse immune response.

The phrase "propensity to develop" refers to likelihood or probability (e.g., greater than about 50, 60, 70, 80, 90, 95, 99 percent) that a subject will present with a condition (e.g., organ rejection).

The phrase "small non-coding RNA" refers to ribonucleic acid sequences, typically less than about 40 nucleotides, and preferably about 17-24 nucleotides, that do not code for proteins, but perform a regulatory function in the cell by regulating gene expression through sequence-specific base-pairing with complementary mRNA sequences. Examples of small non-coding RNA include transfer RNA (tRNA), ribosomal RNA (rRNA), microRNA (miRNA), small nuclear RNA (snRNA), small nucleolar RNA (snoRNA), or signal recognition particle RNA complex (SRP).

The phrase "altered amount of expression" is intended to mean an increase or decrease in expression in a test sample (e.g., obtained from a subject undergoing organ failure) as compared to a reference sample. In certain embodiments, the altered amount of expression is an increase or decrease in nucleic acid expression in a sample as compared to a reference sample.

The term "increases" means a positive alteration. As used herein, "increases" means increases by at least about 5%, for example, about 5, 6, 7, 8, 9, 10, 15, 20, 25, 30, 35, 40, 45, 50, 55, 60, 65, 70, 75, 80, 85, 90, 95, 99 or 100% as compared to the amount in the absence of organ rejection or failure. As used herein, "increases" also means increases by at least about 1-fold, for example, about 1, 2, 3, 4, 5, 6, 7, 8, 9, 10, 15, 20, 30, 40, 50, 60, 70, 80, 90, 100, 200, 500, 1000-fold or more as compared to the amount in the absence of organ rejection or failure.

The term "decreases" means a negative alteration. As used herein, "decreases" means decreases by at least about 5%, for example, about 5, 6, 7, 8, 9, 10, 15, 20, 25, 30, 35, 40, 45, 50, 55, 60, 65, 70, 75, 80, 85, 90, 95, 99 or 100% as compared to the amount in the absence of organ rejection or failure. As used herein, "decreases" also means decreases by at least about 1-fold, for example, about 1, 2, 3, 4, 5, 6, 7, 8, 9, 10, 15, 20, 30, 40, 50, 60, 70, 80, 90, 100, 200, 500, 1000-fold or more as compared to the amount in the absence of organ rejection or failure.

The term "reference" refers to a standard or control condition or parameter.

The term "microarray" refers to a collection of nucleic acid molecules, such as small non-coding RNAs or nucleic acid molecules complementary thereto, affixed to a substrate (e.g., a solid support, chip, plate, or bead). The term can refer to a population of different nucleic acid molecules that are attached to one or more substrates such that the different nucleic acid molecules can be differentiated from each other according to their relative location. An array can include different nucleic acid molecules that are each located at a different identifiable location on a substrate.

The term "nucleic acid" refers to an oligomer or polymer of ribonucleic acid or deoxyribonucleic acid, or analog thereof. This term includes oligomers consisting of naturally occurring bases, sugars, and inter-sugar (backbone) linkages as well as oligomers having non-naturally occurring portions which function similarly. Such modified or substituted oligonucleotides are often preferred over native forms because of properties such as, for example, enhanced stability in the presence of nucleases.

The term "biological sample" is meant to include any sample obtained from a subject. Examples include blood, urine and tissue samples.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The phrase "signal emitting agent" refers to a molecule that gives off a signal used for detection, for example, a signal from a fluorescent label. Examples of fluorescent labels include flourescein, such as fluorescein-12, rhodamine, such as rhodamine 6G (R6G), tetramethylrhodamine (TMR), or alexa flourophores. In preferred embodiments, the signal-emitting agent is a fluorescent label, for example Cy3 or Cy5 fluorescent labels.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified.

The term "identified" as in an "identified profile" refers to one or more compositions or information relating thereto (e.g., a microRNA and its sequence information) obtained under conditions of selection. Such information may optionally be stored by electronic means.

The term "obtaining" as in "obtaining the microRNA rejection score" is intended to include purchasing, synthesizing or otherwise acquiring the microRNA rejection score (or indicated substance or material).

By "mmu-miR134" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 1.

By "mmu-miR144" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 2.

By "mmu-miR466" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 3.

By "mmu-miR7" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 4.

By "mmu-miR346" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 5.

By "mmu-miR468" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 6.

By "mmu-miR188" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 7.

By "mmu-miR298" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 8.

By "mmu-miR467" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 9.

By "mmu-miR292-5p" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 10.

By "mmu-miR186" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 11.

By "mmu-miR486" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 12.

By "mmu-miR451" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 13.

By "mmu-miR18" is meant a microRNA comprising or having at least about 85% 86%, 87%, 88%, 89%, 90%, 91%, 92%, 93%, 94%, 95%, 96%, 97%, 98% or 99% identity to the nucleic acid sequence provided by SEQ ID NO: 14.

By "mmu-miR25" is meant a microRNA comprising or having at least about 85% 86%, 87%, 88%, 89%, 90%, 91%, 92%, 93%, 94%, 95%, 96%, 97%, 98% or 99% identity to the nucleic acid sequence provided by SEQ ID NO: 15.

By "mmu-miR223" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 16.

By "mmu-miR320" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 17.

By "mmu-miR148b" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 18.

By "mmu-miR21" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 19.

By "mmu-miR124a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 20.

By "mmu-miR19a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 21.

By "mmu-miR301" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 22.

By "mmu-miR31" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 23.

By "mmu-miR20" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 24.

By "mmu-miR29c" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 25.

By "mmu-miR148a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 26.

By "mmu-miR17-5p" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 27.

By "mmu-miR185" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 28.

By "mmu-miR106a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 29.

By "mmu-miR106b" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 30.

By "mmu-miR375" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 31.

By "mmu-miR216" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 32.

By "mmu-miR217" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 33.

By "mmu-miR200a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 34.

By "mmu-miR200b" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 35.

By "mmu-miR429" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 36.

By "mmu-miR200c" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 37.

By "mmu-miR141" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 38.

By "mmu-miR148a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 39.

By "mmu-miR152" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 40.

By "mmu-miR182" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 41.

By "mmu-miR99a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 42.

By "mmu-miR130a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 43.

By "mmu-miR127" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 44.

By "mmu-miR100" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 45.

By "mmu-miR199a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 46.

By "mmu-miR199b" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 47.

By "mmu-miR125a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 48.

By "mmu-miR22" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 49.

By "mmu-miR434-3p" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 50.

By "mmu-miR34a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 51.

By "mmu-miR181c" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 52.

By "mmu-miR139" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 53.

By "mmu-miR130a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 54.

By "mmu-miR322" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 55.

By "mmu-miR181a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 56.

By "mmu-miR125a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 57.

By "mmu-miR200b" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 58.

By "mmu-miR145" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 59.

By "mmu-miR127" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 60.

By "mmu-miR199a" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 61.

By "mmu-miR425" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 62.

By "mmu-miR99b" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 63.

By "mmu-let-7e" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 64.

By "mmu-miR195" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 65.

By "mmu-miR152" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 66.

By "mmu-miR125b" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 67.

By "mmu-miR187" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 68.

By "mmu-miR324-3p" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 69.

By "mmu-miR150" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 70.

By "mmu-miR28" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 71.

By "mmu-miR143" is meant a microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NO: 72.

Other definitions appear in context throughout this disclosure.

2. MicroRNAs

MicroRNAs (miRNAs) are a class of small, evolutionary conserved non-coding RNA species contained in the genomes of animals, plants and viruses. As with protein-coding genes, a key to understanding how miRNAs function is to determine when and where they are expressed. miRNAs present unique challenges that make them more difficult to analyze than messenger RNA. The inherent small size of miRNAs provides very little sequence for appending label or for designing probes. miRNAs consist of, for example, about 17-24 nucleotide RNA molecules that regulate the stability or translational efficiency of target mRNAs. To date, several hundred miRNA genes have been identified in a range of animal species, with many of these miRNA genes showing phylogenetic conservation (15). miRNAs have diverse biological functions, and have been shown to play a role in a variety of processes, including development, differentiation, cell death, and cell proliferation, and have also been shown to regulate genes involved in cellular activation and the stress response in a number of species (16). Many microRNAs are located at genomic regions that are linked to cancer (17). Consistent with their role in immune system development, microRNAs have also been implicated in immune defense (17). MicroRNA profiling has recently been used to associate the prognosis and progression of chronic lymphocytic leukemia, as well as to classify human cancers (1-4).

MicroRNAs are highly conserved amongst mammalian species, such as mice and humans (Bartel, D. P. 2004 *Cell* 116:281-297; Lagos-Quintana, et al. 2002 *Current Biology* 12:735-739; Lagos-Quintana, et al. 2003 *Rna-A Publication of the Rna Society* 9:175-179; Lim, L. P., et al. 2003 *Science* 299:1540; Lim, L. P., et al. 2003 *Genes & Development* 17:991-1008).

The degree of conservancy between murine and human microRNA sequences is exemplified in the following sequence alignments (wherein the sequences and sequence numbers can be obtained from the miRBase Sequence database version 10.1 (Sanger Institute, Cambridge, U.K.; http://microrna.sanger.ac.uk/sequences/)):

```
mir-134
mmu-mir-134 (murine, MI0000160):
                                                        (SEQ ID NO: 73)
AGGGUGUGUGACUGGUUGACCAGAGGGGCGUGCACUCUGUUCACCCUGUG

GGCCACCUAGUCACCAACCCU
```

-continued hsa-mir-134 (human, MI0000474)
(SEQ ID NO: 74)
CAGGGUGUGUGACUGGUUGACCAGAGGGGCAUGCACUGUGUUCACCCUGU

GGGCCACCUAGUCACCAACCCUC

```
mouse  1 AGGGTGTGTGACTGGTTGACCAGAGGGGCGTGCACTCTGTTCACCCTGTGGGCCACCTAG 60
         |||||||||||||||||||||||||||| |||||| ||||||||||||||||||||||||
human  2 AGGGTGTGTGACTGGTTGACCAGAGGGGCATGCACTGTGTTCACCCTGTGGGCCACCTAG 61 mouse 61 TCACCAACCCT 71 (SEQ ID NO: 75)
         |||||||||||
human 62 TCACCAACCCT 72 (SEQ ID NO: 76)
``` mir-144
mmu-mir-144 (murine, MI0000168)
(SEQ ID NO: 77)
GGCUGGGAUAUCAUCAUAUACUGUAAGUUUGUGAUGAGACACUACAGUA

UAGAUGAUGUACUAGUC hsa-mir-144 (human, MI0000460)
(SEQ ID NO: 78)
UGGGGCCCUGGCUGGGAUAUCAUCAUAUACUGUAAGUUUGCGAUGAGACA

CUACAGUAUAGAUGAUGUACUAGUCCGGGCACCCCC

```
Mouse  1 GGCTGGGATATCATCATATACTGTAAGTTTGTGATGAGACACTACAGTATAGATGATGTA 60
         ||||||||||||||||||||||||||||| ||||||||||||||||||||||||||||||
Human 10 GGCTGGGATATCATCATATACTGTAAGTTTGCGATGAGACACTACAGTATAGATGATGTA 69

Mouse 61 CTAGTC 66 (SEQ ID NO: 79)
         ||||||
Human 70 CTAGTC 75 (SEQ ID NO: 80)
``` mir-188
mmu-mir-188 (murine, MI0000230)
(SEQ ID NO: 81)
UCUCACAUCCCUUGCAUGGUGGAGGGUGAGCUCUCUGAAAACCCCUCCCA

CAUGCAGGGUUUGCAGGA hsa-mir-188 (human, MI0000484)
(SEQ ID NO: 82)
UGCUCCCUCUCUCACAUCCCUUGCAUGGUGGAGGGUGAGCUUUCUGAAAA

CCCCUCCCACAUGCAGGGUUUGCAGGAUGGCGAGCC

```
Mouse  1 TCTCACATCCCTTGCATGGTGGAGGGTGAGCTCTCTGAAAACCCCTCCCACATGCAGGGT 60
         ||||||||||||||||||||||||||||||| ||||||||||||||||||||||||||||
Human 10 TCTCACATCCCTTGCATGGTGGAGGGTGAGCTTTCTGAAAACCCCTCCCACATGCAGGGT 69

Mouse 61 TTGCAGGA 68 (SEQ ID NO: 83)
         ||||||||
Human 70 TTGCAGGA 77 (SEQ ID NO: 84)
```

The above alignments (using NCBI blast/align 2 (http://www.ncbi.nlm.nih.gov/blast/b12seq/wblast2.cgi) show ≥97% sequence identity.

Thus, included in the invention are small non-coding RNAs or microRNAs. The small non-coding RNAs of the invention consist of about 5-40 nucleotides. Exemplary Thus, included in the invention are small non-coding RNAs or microRNAs. The small non-coding RNAs of the invention consist of about 5-40 nucleotides. Exemplary microRNAs of the invention preferably consist of about 21-23 nucleotides. The small non-coding RNAs of the invention include, but are not limited to, SEQ ID NOs: 1-72. Also included in the invention are small non-coding RNAs or microRNA comprising or having at least about 85%, 86%, 87%, 88%, 89%, 90%, 91%, 92%, 93%, 94%, 95%, 96%, 97%, 98% or 99% identity to the nucleic acid sequence provided by SEQ ID NOs: 1-72.

3. Expression Monitoring and Profiling

According to the invention, organ rejection can be correlated with expression of one or more small RNAs. Thus, the invention provides a method of identifying a subject as having, or having a propensity to develop, organ rejection, monitoring a subject at risk for organ rejection, or diagnosing susceptibility to organ rejection or prognosis of outcome for treatment of organ rejection.

Identifying a subject as having, or having a propensity to develop, organ rejection according to the invention comprises measuring the amount of small non-coding RNA expression in a biological sample from the subject, wherein an altered level of expression relative to a reference indicates that the subject has, or has a propensity to develop, organ rejection.

In specific embodiments, the miRNAs are increased, the increased miRNAs including, but not limited to:

mmu-miR134,
(SEQ ID NO: 1)
UGUGACUGGUUGACCAGAGGGG, mmu-miR144,
(SEQ ID NO: 2)
UACAGUAUAGAUGAUGUACUAG, mmu-miR466,
(SEQ ID NO: 3)
AUACAUACACGCACACAUAAGAC, mmu-miR7,
(SEQ ID NO: 4)
UGGAAGACUAGUGAUUUUGUUG, mmu-miR346,
(SEQ ID NO: 5)
UGUCUGCCCGAGUGCCUGCCUCU, mmu-miR468,
(SEQ ID NO: 6)
UAUGACUGAUGUGCGUGUGUCU, mmu-miR188,
(SEQ ID NO: 7)
CAUCCCUUGCAUGGUGGAGGGU, mmu-miR298,
(SEQ ID NO: 8)
GGCAGAGGAGGGCUGUUCUUCC, mmu-miR-467,
(SEQ ID NO: 9)
AUAUACAUACACACACCUACAC, mmu-miR-292-5p,
(SEQ ID NO: 10)
ACUCAAACUGGGGGCUCUUUUG, mmu-miR-186,
(SEQ ID NO: 11)
CAAAGAAUUCUCCUUUUGGGCUU, mmu-miR-486,
(SEQ ID NO: 12)
UCCUGUACUGAGCUGCCCCGAG, mmu-miR-451,
(SEQ ID NO: 13)
AAACCGUUACCAUUACUGAGUU, mmu-miR-18,
(SEQ ID NO: 14)
UAAGGUGCAUCUAGUGCAGAUA, mmu-miR-25,
(SEQ ID NO: 15)
CAUUGCACUUGUCUCGGUCUGA, mmu-miR-223
(SEQ ID NO: 16)
UGUCAGLTUUGUCAAAUACCCC, mmu-miR-320,
(SEQ ID NO: 17)
AAAAGCUGGGUUGAGAGGGCGAA, mmu-miR-148b,
(SEQ ID NO: 18)
UCAGUGCAUCACAGAACUUUGU, mmu-miR-21,
(SEQ ID NO: 19)
UAGCUUAUCAGACUGAUGUUGA, mmu-miR-124a,
(SEQ ID NO: 20)
UAAGGCACGCGGUGAAUGCC, -continued mmu-miR-19a,
(SEQ ID NO: 21)
UGUGCAAAUCUAUGCAAAACUGA, mmu-miR-301
(SEQ ID NO: 22)
CAGUGCAAUAGUAUUGUCAAAGC, mmu-miR-31,
(SEQ ID NO: 23)
AGGCAAGAUGCUGGCAUAGCUG, mmu-miR-20,
(SEQ ID NO: 24)
UAAAGUGCUUAUAGUGCAGGUAG, mmu-miR-29c,
(SEQ ID NO: 25)
UAGCACCAUUUGAAAUCGGU, mmu-miR-148a,
(SEQ ID NO: 26)
UCAGUGCACUACAGAACUUUGU, mmu-miR-17-5p,
(SEQ ID NO: 27)
CAAAGUGCUUACAGUGCAGGUAGU, mmu-miR-185,
(SEQ ID NO: 28)
UGGAGAGAAAGGCAGUUC, mmu-miR-106a,
(SEQ ID NO: 29)
CAAAGUGCUAACAGUGCAGGUA,
and mmu-miR-106b,
(SEQ ID NO: 30)
UAAAGUGCUGACAGUGCAGAU
and combinations thereof.

In specific embodiments, the miRNAs are decreased, the decreased miRNAs including, but not limited to:

mmu-miR375,
(SEQ ID NO: 31)
UUUGUUCGUUCGGCUCGCGUGA, mmu-miR216,
(SEQ ID NO: 32)
UAAUCUCAGCUGGCAACUGUG, mmu-miR217,
(SEQ ID NO: 33)
UACUGCAUCAGGAACUGACUGGAU, mmu-miR200a,
(SEQ ID NO: 34)
UAACACUGUCUGGUAACGAUGU, mmu-miR200b,
(SEQ ID NO: 35)
UAAUACUGCCUGGUAAUGAUGAC, mmu-miR429,
(SEQ ID NO: 36)
UAAUACUGUCUGGUAAUGCCGU, mmu-miR200c,
(SEQ ID NO: 37)
UAAUACUGCCGGGUAAUGAUGG, mmu-miR141
(SEQ ID NO: 38)
UAACACUGUCUGGUAAAGAUGG, mmu-miR148a,
    (SEQ ID NO: 39)
UCAGUGCACUACAGAACUUUGU, mmu-miR152,
    (SEQ ID NO: 40)
UCAGUGCAUGACAGAACUUGGG, mmu-miR182,
    (SEQ ID NO: 41)
UUUGGCAAUGGUAGAACUCACA, mmu-miR99a,
    (SEQ ID NO: 42)
ACCCGUAGAUCCGAUCUUGU, mmu-miR-130a,
    (SEQ ID NO: 43)
CAGUGCAAUGUUAAAAGGGCAU, mmu-miR-127,
    (SEQ ID NO: 44)
UCGGAUCCGUCUGAGCUUGGC, mmu-miR-100,
    (SEQ ID NO: 45)
AACCCGUAGAUCCGAACUUGUG, mmu-miR-199a,
    (SEQ ID NO: 46)
CCCAGUGUUCAGACUACCUGUUC, mmu-miR-199b,
    (SEQ ID NO: 47)
CCCAGUGUUUAGACUACCUGUUC, mmu-miR-125a,
    (SEQ ID NO: 48)
UCCCUGAGACCCUUUAACCUGUG, mmu-miR-22,
    (SEQ ID NO: 49)
AAGCUGCCAGUUGAAGAACUGU, mmu-miR-434-3p,
    (SEQ ID NO: 50)
UUUGAACCAUCACUCGACUCC, mmu-miR-34a,
    (SEQ ID NO: 51)
UGGCAGUGUCUUAGCUGGUUGUU, mmu-miR-181c,
    (SEQ ID NO: 52)
AACAUUCAACCUGUCGGUGAGU, mmu-miR-139,
    (SEQ ID NO: 53)
UCUACAGUGCACGUGUCU, mmu-miR-130a,
    (SEQ ID NO: 54)
CAGUGCAAUGUUAAAAGGGCAU, mmu-miR-322,
    (SEQ ID NO: 55)
CAGCAGCAAUUCAUGUUUUGGA, mmu-miR-181a,
    (SEQ ID NO: 56)
AACAUUCAACGCUGUCGGUGAGU, mmu-miR-125a,
    (SEQ ID NO: 57)
UCCCUGAGACCCUUUAACCUGUG, mmu-miR-200b,
    (SEQ ID NO: 58)
UAAUACUGCCUGGUAAUGAUGAC, mmu-miR-145,
    (SEQ ID NO: 59)
GUCCAGUUUUCCCAGGAAUCCCUU, mmu-miR-127,
    (SEQ ID NO: 60)
UCGGAUCCGUCUGAGCUUGGC, mmu-miR-199a,
    (SEQ ID NO: 61)
CCCAGUGUUCAGACUACCUGUUC, mmu-miR-425,
    (SEQ ID NO: 62)
AUCGGGAAUGUCGUGUCCGCC, mmu-miR-99b,
    (SEQ ID NO: 63)
CACCCGUAGAACCGACCUUGCG, mmu-let-7e,
    (SEQ ID NO: 64)
UGAGGUAGGAGGUUGUAUAGU, mmu-miR-195,
    (SEQ ID NO: 65)
UAGCAGCACAGAAAUAUUGGC, mmu-miR-152,
    (SEQ ID NO: 66)
UCAGUGCAUGACAGAACUUGGG, mmu-miR-125b,
    (SEQ ID NO: 67)
UCCCUGAGACCCUAACUUGUGA, mmu-miR-187,
    (SEQ ID NO: 68)
UCGUGUCUUGUGUUGCAGCCGG, mmu-miR-324-3p,
    (SEQ ID NO: 69)
CCACUGCCCCAGGUGCUGCUGG, mmu-miR-150,
    (SEQ ID NO: 70)
UCUCCCAACCCUUGUACCAGUG, mmu-miR-28,
    (SEQ ID NO: 71)
AAGGAGCUCACAGUCUAUUGAG,
and mmu-miR-143
    (SEQ ID NO: 72)
UGAGAUGAAGCACUGUAGCUCA, and combinations thereof.

4. miRNA Detection and Analysis

While Northern blots are frequently used for miRNA analysis, improvements and adaptations to existing technologies have also been tailored to small RNA detection. These include oligonucleotide filter macroarrays, RNA oligonucleotide ligation followed by RT-PCR amplification, fluorescence resonance energy transfer, signal-amplifying ribozymes, primer extension, nuclease protection assay, and various microarray-based methods.

In one particular example, the amount of expression is determined using a microarray. A microarray is used according to the invention as a tool for analyzing microRNA expression. A microarray consists of samples of many genes arranged in a regular pattern. Preferably, the microarray can be a chip, a bead, or a membrane.

The nucleic acid molecules or polypeptides of the invention are useful as hybridizable array elements in a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

To produce a nucleic acid microarray, oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, preferably as a bodily fluid (such as blood, cerebrospinal fluid, phlegm, saliva, or urine) or tissue sample (e.g. a tissue sample obtained by biopsy). For some applications, cultured cells (e.g., lymphocytes) or other tissue preparations may be used. The mRNA is isolated according to standard methods, and cDNA is produced and used as a template to make complementary RNA suitable for hybridization. Such methods are described herein. The RNA is amplified in the presence of fluorescent nucleotides, and the labeled probes are then incubated with the microarray to allow the probe sequence to hybridize to complementary oligonucleotides bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and still more preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a still more preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and more preferably less than about 15 mM NaCl and 1.5 mM trisodium citrate. Stringent temperature conditions for the wash steps will ordinarily include a temperature of at least about 25° C., more preferably of at least about 42° C., and more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a still more preferred embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct sequences simultaneously (e.g., Heller et al., Proc. Natl. Acad. Sci. 94:2150-2155, 1997). Preferably, a scanner is used to determine the levels and patterns of fluorescence.

Proteins may also be analyzed using protein microarrays. Such arrays are useful in high-throughput low-cost screens to identify peptide or candidate compounds that bind a polypeptide, or fragment thereof. Typically, protein microarrays feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins (e.g., polypeptides encoded by a nucleic acid molecule listed in Table 2 or Table 4 or antibodies against such polypeptides) are spotted on a substrate using any convenient method known to the skilled artisan (e.g., by hand or by inkjet printer). Preferably, such methods retain the biological activity or function of the protein bound to the substrate (Ge et al., supra; Zhu et al., supra).

The protein microarray is hybridized with a detectable probe. Such probes can be polypeptide, nucleic acid, or small molecules. For some applications, polypeptide and nucleic acid probes are derived from a biological sample taken from a patient, such as a bodily fluid (such as blood, urine, saliva, or phlegm); a homogenized tissue sample (e.g. a tissue sample obtained by biopsy); or cultured cells (e.g., lymphocytes). Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Microarrays are commercially available, for example from Ambion (on the world wide web at ambion.com) and LC Sciences (on the world wide web at lcsciences.com). Such commercially available microarray platforms offer a genome-wide microRNA expression profiling service utilizing a microarray detection system that was developed specifically for microRNA detection. Commercial services such as these will perform all the functions and analysis from sample QC through data analysis on the total RNA sample of interest. Further, these commercial services will perform microarray analysis on a single sample to create a simple expression profile or hybridize two samples to the same microarray for a "dual sample" analysis, which is useful to the present invention, for example, when comparison of two samples is needed.

The invention further provides methods for monitoring a subject at risk for organ rejection (e.g., a transplantation recipient), comprising determining the amount of small non-coding RNA expression in a biological sample obtained from the subject, where an altered amount of expression relative to a reference indicates that the subject has, or has a propensity to develop, organ rejection. The organ rejection can occur at any time after transplantation. In preferred embodiments of the invention, the method monitors cardiac transplantation.

Methods of the invention can include obtaining an organ rejection score. Such a score can be obtained by collecting a sample of RNA from subjects with organ rejection, isolating and purifying microRNA from the sample, labeling the microRNAs with a signal emitting agent, hybridizing the microRNAs to substrates containing oligonucleotides that are complementary to the microRNAs, detecting the signal for each hybridized microRNA, calculating an average value between the detected signals and a reference signal; and obtaining a ratio of the signal between sample and reference, thereby obtaining an organ rejection score. In a particular embodiment of the method, the ratio is obtained according to the following method. Twenty micrograms of total RNA is isolated and small RNAs (<200 nt) are isolated from polyacrylamide gels. The RNAs are processed and used for microarray analyses. Briefly, purified small RNAs are labeled with Cy3 or Cy5 fluorescent dyes (one dye for control, the other for 'acute rejection' samples) and hybridized to dual-channel microarray ParaFlo microfluidics chips (LC Sciences). Each of the detection probes spots a nucleotide sequence complementary to a specific miRNA sequence and a long nonnucleotide molecule spacer that extends the specific sequence away from the chip surface. The miRNA probe sequences can be obtained from the miRBase Sequence database version 7.1 (Sanger Institute, Cambridge, U.K.; http: microrna.sanger.ac.uk sequences). Each probe spot measured is 100 pixels, and only those spots whose pixel intensities had a standard deviation of 0.001 are accepted. The data are then corrected by subtracting the background and normalizing to the statistical median of all detectable transcripts. Microarray experiments can be performed twice with one pair of RNA samples and once with the other pair.

In one example of the method, the microRNA is isolated and purified from the sample and labeled with a signal emitting agent. The signal emitting agent can be a fluorescent label. In a specific example, the microRNA is fluorescently hybridized with Cy3 or Cy5. Other examples of fluorescent labels include flourescein, such as fluorescein-12, rhodamine, such as rhodamine 6G (R6G), tetramethyl-rhodamine (TMR), or alexa flourophores. Other examples of signal emitting agents include, but are not limited to, mass, electrical conductivity or other optical signals such absorption signal, luminescent signal, chemiluminescent signal or the like.

As used herein, the term "reference," as in reference level or signal, refers to a standard or control condition or parameter. In particular embodiments of the invention, the reference level is used to determine an organ rejection score. For example, the reference level may be a readout of the signal detected that indicates microRNA expression for a control sample, e.g. an organ that has not been transplanted. The reference level allows quantification of difference between control and test sample. Thus, the reference allows comparison of microRNA expression. For example, when the level of one or more microRNAs in a test sample or subject (e.g. a transplant recipient) are higher than the reference level of one or more microRNAs in a reference sample the cells will be considered to have a high level of expression of the one or more microRNAs. Conversely, when the level of one or more microRNAs in test sample or subject (e.g. a transplant recipient) are lower than the reference level of one or more microRNAs, the cells will be considered to have a low level of expression, or underproduction, of the one or more microRNAs. A reference level can also represent the levels of two or more small RNAs.

In particular, the methods of the invention are useful for determining if a patient is at risk for organ rejection following transplantation. Because there is emerging evidence for 'clinical rejection' despite 'normal' pathologic specimens, dysregulation occurring at the molecular level is believed to precede the onset of cellular rejection. Accordingly, methods of the invention can be used to identify a molecular signature consisting of small microRNAs to distinguish normal transplant tissue from tissue undergoing rejection at an earlier stage. For example, the methods of the invention can be used to distinguish normal peripheral blood immune cells from 'rejecting' immune cells in patients that have undergone transplantation.

Organ rejection can occur anytime following transplantation, as such rejection is a lifelong process. In a specific embodiment, organ rejection can occur in about 1, 2, 3, 4, 5, 6, or more days following transplantation. In another specific embodiment, organ rejection can occur in about 1, 2, 3 or more weeks following transplantation. In yet another specific embodiment, organ rejection can occur in about 1, 2, 3, 4, 5, 6, 7, 8, 9, 10, 11, or more months following transplantation. In yet another specific embodiment, organ rejection can occur in about 1, 2, 3, 4, 5, or more years following transplantation. Methods of the invention for use in detecting organ rejection can be applied at any time post-transplantation, and in specific embodiments, at the times indicated herein.

The methods of the invention also are useful for determining a proper course of treatment for a patient at risk for organ rejection. In particular, the methods of the invention can be used for a cardiac transplant patient. A course of treatment refers to the therapeutic measures taken for a patient after organ transplantation and/or immunosuppressive therapy. For example, a determination of the likelihood for organ rejection can assist in determining whether a more conservative or more radical approach to immunotherapy should be taken, or whether treatment modalities should be combined. In another example, the prognostic methods of the invention can be used to identify transplant candidates likely to experience rejection so that they can be offered additional therapeutic options.

For example, levels of microRNA can be compared for cells that are treated and untreated with a particular agent to determine effect of the agent on microRNA expression. For example, the levels of microRNA might be evaluated before, or at any time, during immunosuppressive drug therapy. Thus, the level of a microRNA can be quantitated in the same cells at different times before, during or after exposure to particular conditions or agents.

5. Biological Samples

The biological samples are generally derived from a subject, preferably as a bodily fluid, such as blood cells, biopsy specimens, urine cells/urine sediment, or cells found in sputum, or tissue sample (e.g. a tissue sample obtained by biopsy). In particular, the blood cells can be peripheral blood mononuclear cells. In an exemplary embodiment, the blood cells are leukocytes. Leukocytes are preferably obtained from the spleen. A biological sample can be from a normal subject or a subject displaying one or more symptoms of a particular disease or condition. Thus, a biological sample can be obtained from an organ undergoing rejection, or from a subject experiencing a condition set forth below. A biological sample can be obtained from a subject at different time points. Thus, a biological sample used in a method of the invention can be obtained from a subject prior to undergoing organ transplantation, at any time point after organ transplantation.

Those skilled in the art will know or be able to readily determine methods for isolating nucleic acid samples from a cell, fluid or tissue using methods known in the art such as those described in Sambrook et al., Molecular Cloning: A Laboratory Manual, 3rd edition, Cold Spring Harbor Laboratory, New York (2001) or in Ausubel et al., Current Protocols in Molecular Biology, John Wiley and Sons, Baltimore, Md. (1998).

6. Kits

The invention provides kits for the diagnosis of a subject having, or having a propensity to develop, organ rejection, the kits comprising at least one nucleic acid molecule complementary to a small non-coding RNA of the invention. In one embodiment, the kit further comprises an adsorbent that retains at least one small non-coding RNA molecule.

The kit includes written instructions for use in detection of organ rejection. The kit includes directions for diagnosis of a subject having, or having a propensity to develop, organ rejection. Optionally, the kit comprises a sterile container that contains the detection regents; such containers can be boxes, ampoules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the reagents described herein and their use in detection of organ rejection. Preferably, the kit further comprises any one or more of the reagents described in the diagnostic assays described herein. In other embodiments, the instructions include at least one of the following: description of the miRNA; methods for using the enclosed materials for the detection of organ rejection; precautions; warnings; indications; clinical or research studies; and/or references. The instructions may be printed directly on the container (when present), or as a label applied to the container, or as a separate sheet, pamphlet, card, or folder supplied in or with the container.

EXAMPLES

Each year endomyocardial biopsies (EMB) are performed on thousands of patients worldwide (~100,000 visits) for diagnosing rejection after cardiac transplantation. While endomyocardial biopsy remains the gold standard, it is a costly and invasive procedure, and causes patient discomfort, and poses a low risk of morbidity and death. Furthermore, endomyocardial biopsy suffers from sampling error and variable, subjective pathological interpretation. In addition, while over ~75% of biopsies are negative for rejection, there is emerging evidence for 'clinical rejection' despite 'normal' pathologic cardiac specimens indicating that dysregulation that occurs at the molecular level precedes the onset of cardiac cellular rejection.

Example 1: Differential Regulation of MicroRNA Expression Associated with Organ Rejection MicroRNAs are highly conserved across species, especially human, mouse, and rat. Thus, in order to minimize biological variation and maximize reproducibility of experimental results, the mouse heterotopic cardiac transplantation model presents an attractive model system to study microRNA expression.

Figure 1B:
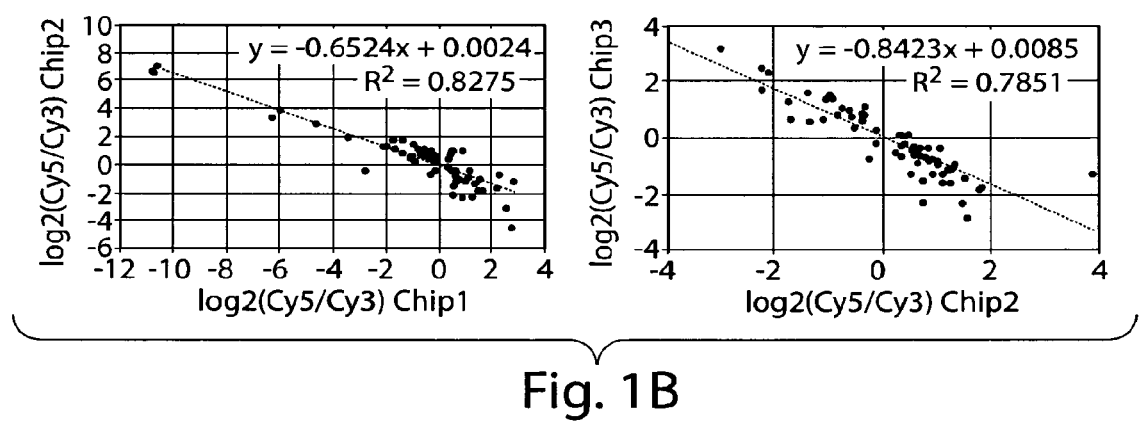
FIG. 1B shows two graphs. The graphs are a plot of the Cy3/Cy5 ratio compared between two chips (control and rejection) on a log scale to reflect log-fold differences between samples.

To verify the existence of differentially expressed microRNAs from leukocytes of mice with and without cardiac resection, three sets of total RNA were harvested from spleens, a leukocyte-rich organ, after heterotopic cardiac transplantation. MicroRNA was isolated, purified, and then fluorescently hybridized with Cy3 or Cy5 fluorescent labels to mouse microRNA chips containing a total of 464 oligonucleotides for mature or pre-microRNAs (LC Sciences, Houston, Tex.). Each signal represents the average of the same microRNA oligo (n=6) that was separately spotted (FIGS. 1, A and B). From this data, a ratio of Cy3/Cy5 is calculated that reflects the log-fold differences between the two samples for a given microRNA. In an exemplary embodiment, for example, small RNAs were labeled with Cy3 or Cy5 fluorescent dyes (one dye for control, the other for 'acute rejection' samples) and hybridized to dual-channel microarray ParaFlo microfluidics chips (LC Sciences). Each of the detection probes spotted a nucleotide sequence complementary to a specific miRNA sequence and a long nonnucleotide molecule spacer that extended the specific sequence away from the chip surface. Each microarray chip contained six probe sets. Each probe spot measured was 100 pixels, and only those spots whose pixel intensities had a standard deviation of 0.001 were accepted. The data were corrected by subtracting the background and normalizing to the statistical median of all detectable transcripts. As indicated previously, microarray experiments were performed twice with one pair of RNA samples and once with the other pair. Table 1, below, lists 96 microRNAs that are differentially expressed at $P<0.01$. Table 2, below, lists 20 of the 96 microRNAs that are differentially expressed at $P<0.01$. These 20 microRNAs are comparatively more predictive in the setting of organ rejection. FIG. 1B shows that the differential microRNA expression pattern across chips is highly reproducible, with correlation coefficients ranging from $R^2=0.7851$ to 0.8275 for all microRNAs, $P<0.01$.

Some of the microRNAs identified have been reported to target important genes in cellular activation, growth, and differentiation. One microRNA, mmu-miR-375, (designated as No. 1 on Table 2) was decreased in rejection samples by ~1726-fold. Mmu-miR-375 represses the protein myotrophin (MPTN), a gene induced in failing human hearts that can also directly modulate levels of p50/p65. p50/p65 are two members of the NF-kB family critical for cellular activation (6). Thus, this finding suggests that a deficiency of mmu-miR-375 may allow for the induction of MPTN expression and accelerated inflammation. Additional microRNAs identified that have known biological functions include: mmu-miR-148a, which targets Hox5A and regulates p53, mmu-miR-298, which targets PTEN to regulate AKT), and mmmu-miR-223, which targets NFI-A to regulate granulocytic differentiation. Taken together, this data shows that specific microRNAs, such as mmu-miR-375, mmu-miR-148a, and mmmu-miR-223, are differentially regulated in the setting of rejection. This data indicates the existence of a microRNA leukocyte signature that is dynamically associated with inflammation.

TABLE 1

Differentially regulated microRNAs
(rejection vs control (P < 0.01))

| No. | Probe_ID | WT Ctrl | Rejection | Log2 (Sample B/ Sample A) |
|---|---|---|---|---|
| 1 | mmu-miR-375 | 2,796.60 | 1.62 | −10.80 |
| 2 | mmu-miR-216 | 8,640.60 | 5.02 | −10.68 |
| 3 | mmu-miR-217 | 4,202.86 | 2.67 | −10.63 |
| 4 | mmu-miR-200a | 3,227.50 | 38.34 | −6.33 |
| 5 | mmu-miR-200b | 4,544.34 | 76.99 | −5.99 |
| 6 | mmu-miR-429 | 525.10 | 20.47 | −4.69 |
| 7 | mmu-miR-200c | 5,627.92 | 533.36 | −3.45 |
| 8 | mmu-miR-141 | 119.46 | 14.48 | −3.13 |
| 9 | mmu-miR-134 | 78.25 | 550.25 | 2.84 |
| 10 | mmu-miR-148a | 29,783.96 | 4,384.91 | −2.76 |
| 11 | mmu-miR-144 | 25.59 | 190.38 | 2.74 |
| 12 | mmu-miR-466 | 23.99 | 164.73 | 2.65 |
| 13 | mmu-miR-7 | 346.06 | 2,098.99 | 2.56 |
| 14 | mmu-miR-346 | 21.54 | 138.99 | 2.54 |
| 15 | mmu-miR-468 | 27.98 | 146.81 | 2.53 |
| 16 | mmu-miR-188 | 205.16 | 969.29 | 2.30 |
| 17 | mmu-miR-152 | 5,299.79 | 1,086.64 | −2.19 |
| 18 | mmu-miR-298 | 104.12 | 474.59 | 2.19 |
| 19 | mmu-miR-182 | 296.80 | 71.81 | −1.98 |
| 20 | mmu-miR-99a | 4,410.42 | 1,248.83 | −1.81 |
| 21 | mmu-miR-467 | 58.38 | 231.79 | 1.78 |
| 22 | mmu-miR-130a | 7,011.46 | 2,195.77 | −1.68 |
| 23 | mmu-miR-292-5p | 1,002.17 | 3,007.66 | 1.62 |
| 24 | mmu-miR-186 | 361.75 | 1,094.36 | 1.55 |
| 25 | mmu-miR-486 | 1,635.36 | 4,205.21 | 1.46 |
| 26 | mmu-miR-127 | 326.09 | 121.91 | −1.42 |
| 27 | mmu-miR-100 | 2,856.59 | 1,072.46 | −1.40 |
| 28 | Mmu-miR-451 | 26,948.82 | 67,199.76 | 1.32 |
| 29 | Mmu-miR-18 | 509.93 | 1,174.74 | 1.26 |
| 30 | Mmu-miR-25 | 3,575.44 | 8,550.36 | 1.26 |
| 31 | Mmu-miR-223 | 3,453.25 | 7,984.72 | 1.20 |
| 32 | Mmu-miR-199a | 4,827.74 | 2,274.21 | −1.12 |
| 33 | Mmu-miR-199b | 2,338.46 | 1,141.34 | −1.09 |
| 34 | Mmu-miR-320 | 3,951.96 | 8,389.89 | 1.08 |
| 35 | Mmu-miR-125a | 8,344.75 | 4,412.97 | −1.03 |
| 36 | Mmu-miR-148b | 546.18 | 1,170.21 | 1.00 |
| 37 | Mmu-miR-22 | 10,046.84 | 4,750.97 | −1.00 |
| 38 | Mmu-miR-434-3p | 380.84 | 189.60 | −0.99 |
| 39 | Mmu-miR-34a | 1,033.47 | 525.40 | −0.94 |
| 40 | Mmu-miR-21 | 20,551.74 | 38,697.55 | 0.94 |
| 41 | Mmu-miR-181c | 593.20 | 296.90 | −0.94 |
| 42 | Mmu-miR-99b | 3,403.22 | 1,830.55 | −0.90 |
| 43 | Mmu-miR-151 | 218.77 | 395.72 | 0.88 |
| 44 | Mmu-miR-301 | 457.30 | 815.52 | 0.84 |
| 45 | Mmu-miR-145 | 29,272.02 | 16,082.57 | −0.83 |
| 46 | Mmu-miR-125b | 13,470.92 | 7,637.94 | −0.82 |
| 47 | Mmu-miR-20 | 10,347.20 | 17,790.35 | 0.80 |
| 48 | Mmu-miR-143 | 18,960.94 | 10,575.46 | −0.80 |
| 49 | Mmu-miR-181a | 14,532.91 | 8,671.34 | −0.73 |
| 50 | Mmu-miR-185 | 2,900.34 | 4,396.69 | 0.64 |
| 51 | Mmu-miR-142-3p | 1,799.38 | 2,778.87 | 0.63 |
| 52 | Mmu-miR-126-3p | 23,948.67 | 16,008.05 | −0.59 |
| 53 | Mmu-miR-17-5p | 12,514.82 | 18,339.27 | 0.58 |
| 54 | Mmu-miR-23a | 23,207.18 | 15,615.82 | −0.57 |
| 55 | Mmu-miR-106a | 7,001.21 | 9,913.03 | 0.57 |
| 56 | Mmu-miR-24 | 16,342.98 | 11,038.96 | −0.57 |
| 57 | Mmu-miR-93 | 6,735.00 | 9,551.19 | 0.56 |
| 58 | Mmu-miR-195 | 11,202.71 | 7,795.37 | −0.56 |
| 59 | Mmu-miR-221 | 4,347.18 | 6,418.13 | 0.55 |
| 60 | Mmu-miR-290 | 3,014.37 | 4,337.68 | 0.55 |
| 61 | mmu-miR-199a* | 8,969.10 | 6,338.21 | −0.55 |
| 62 | mmu-miR-29c | 3,365.70 | 2,304.60 | −0.55 |

TABLE 1-continued

Differentially regulated microRNAs
(rejection vs control (P < 0.01))

| No. | Probe_ID | WT Ctrl | Rejection | Log2 (Sample B/ Sample A) |
|---|---|---|---|---|
| 63 | mmu-miR-23b | 24,429.36 | 16,820.77 | −0.54 |
| 64 | mmu-miR-92 | 8,318.43 | 11,862.64 | 0.52 |
| 65 | mmu-miR-19a | 1,702.33 | 2,432.34 | 0.51 |
| 66 | mmu-miR-101a | 2,795.12 | 2,141.54 | −0.50 |
| 67 | mmu-miR-324-5p | 665.56 | 474.16 | −0.49 |
| 68 | mmu-let-7b | 23,243.38 | 16,632.63 | −0.49 |
| 69 | mmu-miR-424 | 1,235.91 | 1,712.95 | 0.48 |
| 70 | mmu-miR-30c | 23,043.20 | 15,913.93 | −0.47 |
| 71 | mmu-miR-98 | 4,053.61 | 5,642.67 | 0.44 |
| 72 | mmu-miR-30b | 20,837.35 | 14,935.67 | −0.42 |
| 73 | mmu-miR-106b | 7,710.73 | 10,271.22 | 0.41 |
| 74 | mmu-miR-17-3p | 711.64 | 943.97 | 0.41 |
| 75 | mmu-miR-342 | 8,793.40 | 11,718.79 | 0.39 |
| 76 | mmu-miR-181b | 4,095.46 | 3,222.04 | −0.35 |
| 77 | mmu-miR-30e | 6,598.59 | 7,782.69 | 0.34 |
| 78 | mmu-miR-27a | 10,562.81 | 7,979.07 | −0.33 |
| 79 | mmu-miR-222 | 2,343.61 | 2,955.75 | 0.33 |
| 80 | mmu-miR-27b | 12,223.70 | 9,357.25 | −0.33 |
| 81 | mmu-miR-29b | 11,935.48 | 9,499.93 | −0.31 |
| 82 | mmu-miR-361 | 4,993.90 | 4,009.91 | −0.31 |
| 83 | mmu-miR-26a | 33,714.99 | 27,005.08 | −0.31 |
| 84 | mmu-miR-15b | 16,445.03 | 19,901.34 | 0.29 |
| 85 | mmu-miR-15a | 11,141.45 | 14,065.78 | 0.29 |
| 86 | mmu-let-7c | 28,882.94 | 23,380.52 | −0.29 |
| 87 | mmu-let-7d | 27,591.51 | 22,585.14 | −0.29 |
| 88 | mmu-miR-16 | 33,280.97 | 39,569.63 | 0.27 |
| 89 | mmu-miR-155 | 6,820.70 | 8,592.81 | 0.26 |
| 90 | mmu-miR-150 | 31,416.60 | 26,536.55 | −0.25 |
| 91 | mmu-miR-146 | 20,864.45 | 17,931.99 | −0.20 |
| 92 | mmu-miR-29a | 30,320.91 | 26,260.37 | −0.18 |
| 93 | mmu-let-7a | 32,391.24 | 27,845.77 | −0.16 |
| 94 | mmu-miR-19b | 13,696.95 | 11,581.14 | −0.16 |
| 95 | mmu-miR-30a-5p | 10,754.31 | 9,744.03 | −0.15 |
| 96 | mmu-let-7g | 24,316.37 | 22,311.07 | −0.13 |

TABLE 2

Twenty differentially regulated microRNAs
(rejection vs.controls (P < 0.01))

| No. | MicroRNA | WT | Rejection | Signal log2 (WT/Rejection) |
|---|---|---|---|---|
| 1 | mmu-miR-375 | 2796.60 | 1.62 | −10.80 |
| 2 | mmu-miR-216 | 8640.60 | 5.02 | −10.68 |
| 3 | mmu-miR-217 | 4202.86 | 2.67 | −10.63 |
| 4 | mmu-miR-200a | 3227.50 | 38.34 | −6.33 |
| 5 | mmu-miR-200b | 4544.34 | 76.99 | −5.99 |
| 6 | mmu-miR-429 | 525.10 | 20.47 | −4.69 |
| 7 | mmu-miR-200c | 5627.92 | 533.36 | −3.45 |
| 8 | mmu-miR-141 | 119.46 | 14.48 | −3.13 |
| 9 | mmu-miR-134 | 78.25 | 550.25 | 2.84 |
| 10 | mmu-miR-148a | 29,783.96 | 4,384.91 | −2.76 |
| 11 | mmu-miR-144 | 25.59 | 190.38 | 2.74 |
| 12 | mmu-miR-466 | 23.99 | 164.73 | 2.65 |
| 13 | mmu-miR-7 | 346.06 | 2098.99 | 2.56 |
| 14 | mmu-miR-346 | 21.54 | 138.99 | 2.54 |
| 15 | mmu-miR-468 | 27.98 | 146.81 | 2.53 |
| 16 | mmu-miR-188 | 205.15 | 969.29 | 2.30 |
| 17 | mmu-miR-152 | 5299.79 | 1086.64 | −2.19 |
| 18 | mmu-miR-298 | 104.12 | 474.59 | 2.19 |
| 19 | mmu-miR-182 | 296.8 | 71.81 | −1.98 |
| 20 | mmu-miR-99a | 4410.42 | 1248.83 | −1.81 |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, patent applications, and publications mentioned in this specification are herein incorporated by reference to the same extent as if each independent patent, patent application and publication was specifically and individually indicated to be incorporated by reference.

REFERENCES

1. Volinia, S., Calin, G. A., Liu, C. G., Ambs, S., Cimmino, A., Petrocca, F., Visone, R., Iorio, M., Roldo, C., Ferracin, M., et al. 2006. A microRNA expression signature of human solid tumors defines cancer gene targets. Proc Natl Acad Sci USA.
2. Calin, G. A., Ferracin, M., Cimmino, A., Di Leva, G., Shimizu, M., Wojcik, S. E., Iorio, M. V., Visone, R., Sever, N. I., Fabbri, M., et al. 2005. A MicroRNA signature associated with prognosis and progression in chronic lymphocytic leukemia. N Engl J Med 353:1793-1801.
3. Lu, J., Getz, G., Miska, E. A., Alvarez-Saavedra, E., Lamb, J., Peck, D., Sweet-Cordero, A., Ebert, B. L., Mak, R. H., Ferrando, A. A., et al. 2005. MicroRNA expression profiles classify human cancers. Nature 435:834-838.
4. Febbo, P. G., Thorner, A., Rubin, M. A., Loda, M., Kantoff, P. W., Oh, W. K., Golub, T., and George, D. 2006. Application of oligonucleotide microarrays to assess the biological effects of neoadjuvant imatinib mesylate treatment for localized prostate cancer. Clin Cancer Res 12:152-158.
5. Deng, M. C., Eisen, Hi., Mehra, M. R., Billingham, M., Marboe, C. C., Berry, G., Kobashigawa, J., Johnson, F. L., Starling, R. C., Murali, S., et al. 2006. Noninvasive discrimination of rejection in cardiac allograft recipients using gene expression profiling. Am J Transplant 6:150-160.
6. Knuefermann, P., Chen, P., Misra, A., Shi, S. P., Abdellatif, M., and Sivasubramanian, N. 2002. Myotrophin/V-1, a protein up-regulated in the failing human heart and in postnatal cerebellum, converts NFkappa B p50-p65 heterodimers to p50-p50 and p65-p65 homodimers. J Biol Chem 277:23888-23897.
7. Feinberg, M. W., Shimizu, K., Lebedeva, M., Haspel, R., Takayama, K., Chen, Z., Frederick, J. P., Wang, X. F., Simon, D. I., Libby, P., et al. 2004. Essential role for Smad3 in regulating MCP-1 expression and vascular inflammation. Circ Res 94:601-608.
8. Corry, R. J., Winn, H. J., and Russell, P. S. 1973. Primarily vascularized allografts of hearts in mice. The role of H-2D, H-2K, and non-H-2 antigens in rejection. Transplantation 16:343-350.
9. Shimizu, K., Schonbeck, U., Mach, F., Libby, P., and Mitchell, R. N. 2000. Host CD40 ligand deficiency induces long-term allograft survival and donor-specific tolerance in mouse cardiac transplantation but does not prevent graft arteriosclerosis. Journal of Immunology 165:3506-3518.
10. Sebastiani, P., Gussoni, E., Kohane, I. S., and Ramoni, M. F. 2003. Statistical challenges in functional genomics. Statistical Science 18:33-70.
11. Sebastiani, P., Yu, Y. H., and Ramoni, M. F. 2003. Bayesian machine learning and its potential applications to the genomic study of oral oncology. Adv Dent Res 17:104-108.
12. Ramoni, M. F., Sebastiani, P., and Kohane, I. S. 2002. Cluster analysis of gene expression dynamics. Proc Natl Acad Sci USA 99:9121-9126.
13. Stewart, S., Winters, G. L., Fishbein, M. C., Tazelaar, H. D., Kobashigawa, J., Abrams, J., Andersen, C. B., Angelini, A., Berry, G. J., Burke, M. M., et al. 2005. Revision of the 1990 working formulation for the standardization of nomenclature in the diagnosis of heart rejection. J Heart Lung Transplant 24:1710-1720.
14. Billingham, M., and Kobashigawa, J. A. 2005. The revised ISHLT heart biopsy grading scale. J Heart Lung Transplant 24:1709.
15. Ambros, V. 2004. The functions of animal microRNAs. Nature 431(7006): 350-355.
16. Labourier E. et al. 2005. An optimized isolation and labeling platform for accurate microRNA expression profiling. RNA. 11:1461-1470.
17. Miska, E. A. and Alvarez-Garcia, I. 2005. MicroRNA functions in animal development and human disease. Development. 132. 4653-464662.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

---

What is claimed is:

1. A method for identifying a subject as having, or having a propensity to develop, organ rejection, the method comprising:
   (i) transplanting an allogeneic organ into a subject in need thereof,
   (ii) measuring the expression of at least 20 miRNAs selected from the group consisting of:

mmu-miR-134, (SEQ ID NO: 1)
UGUGACUGGUUGACCAGAGGGG, mmu-miR-144, (SEQ ID NO: 2)
UACAGUAUAGAUGAUGUACUAG, mmu-miR-466, (SEQ ID NO: 3)
AUACAUACACGCACACAUAAGAC, mmu-miR-7, (SEQ ID NO: 4)
UGGAAGACUAGUGAUUUUGUUG, -continued mmu-miR-346,
(SEQ ID NO: 5)
UGUCUGCCCGAGUGCCUGCCUCU, mmu-miR-468,
(SEQ ID NO: 6)
UAUGACUGAUGUGCGUGUGUCU, mmu-miR-188,
(SEQ ID NO: 7)
CAUCCCUUGCAUGGUGGAGGGU, mmu-miR-298,
(SEQ ID NO: 8)
GGCAGAGGAGGGCUGUUCUUCC, mmu-miR-467,
(SEQ ID NO: 9)
AUAUACAUACACACACCUACAC, mmu-miR-292-5p,
(SEQ ID NO: 10)
ACUCAAACUGGGGGCUCUUUUG, mmu-miR-186,
(SEQ ID NO: 11)
CAAAGAAUUCUCCUUUUGGGCUU, mmu-miR-486,
(SEQ ID NO: 12)
UCCUGUACUGAGCUGCCCCGAG, mmu-miR-451,
(SEQ ID NO: 13)
AAACCGUUACCAUUACUGAGUU, mmu-miR-18,
(SEQ ID NO: 14)
UAAGGUGCAUCUAGUGCAGAUA, mmu-miR-25,
(SEQ ID NO: 15)
CAUUGCACUUGUCUCGGUCUGA, mmu-miR-223
(SEQ ID NO: 16)
UGUCAGUUUGUCAAAUACCCC, mmu-miR-320,
(SEQ ID NO: 17)
AAAAGCUGGGUUGAGAGGGCGAA, mmu-miR-148b,
(SEQ ID NO: 18)
UCAGUGCAUCACAGAACUUUGU, mmu-miR-21,
(SEQ ID NO: 19)
UAGCUUAUCAGACUGAUGUUGA, mmu-miR-124a,
(SEQ ID NO: 20)
UAAGGCACGCGGUGAAUGCC, mmu-miR-19a,
(SEQ ID NO: 21)
UGUGCAAAUCUAUGCAAAACUGA, mmu-miR-301
(SEQ ID NO: 22)
CAGUGCAAUAGUAUUGUCAAAGC, mmu-miR-31,
(SEQ ID NO: 23)
AGGCAAGAUGCUGGCAUAGCUG, mmu-miR-20,
(SEQ ID NO: 24)
UAAAGUGCUUAUAGUGCAGGUAG, -continued mmu-miR-29c,
(SEQ ID NO: 25)
UAGCACCAUUUGAAAUCGGU, mmu-miR-148a,
(SEQ ID NO: 26)
UCAGUGCACUACAGAACUUUGU, mmu-miR-17-5p,
(SEQ ID NO: 27)
CAAAGUGCUUACAGUGCAGGUAGU, mmu-miR-185,
(SEQ ID NO: 28)
UGGAGAGAAAGGCAGUUC, mmu-miR-106a,
(SEQ ID NO: 29)
CAAAGUGCUAACAGUGCAGGUA, mmu-miR-106b,
(SEQ ID NO: 30)
UAAAGUGCUGACAGUGCAGAU, mmu-miR-375,
(SEQ ID NO: 31)
UUUGUUCGUUCGGCUCGCGUGA, mmu-miR-216,
(SEQ ID NO: 32)
UAAUCUCAGCUGGCAACUGUG, mmu-miR-217,
(SEQ ID NO: 33)
UACUGCAUCAGGAACUGACUGGAU, mmu-miR-200a,
(SEQ ID NO: 34)
UAACACUGUCUGGUAACGAUGU, mmu-miR-200b,
(SEQ ID NO: 35)
UAAUACUGCCUGGUAAUGAUGAC, mmu-miR-429,
(SEQ ID NO: 36)
UAAUACUGUCUGGUAAUGCCGU, mmu-miR-200c,
(SEQ ID NO: 37)
UAAUACUGCCGGGUAAUGAUGG, mmu-miR-141
(SEQ ID NO: 38)
UAACACUGUCUGGUAAAGAUGG, mmu-miR-148a,
(SEQ ID NO: 39)
UCAGUGCACUACAGAACUUUGU, mmu-miR-152,
(SEQ ID NO: 40)
UCAGUGCAUGACAGAACUUGGG, mmu-miR-182,
(SEQ ID NO: 41)
UUUGGCAAUGGUAGAACUCACA, mmu-miR-99a,
(SEQ ID NO: 42)
ACCCGUAGAUCCGAUCUUGU, mmu-miR-130a,
(SEQ ID NO: 43)
CAGUGC AAUGUU AAAAGGGC AU, mmu-miR-127,
(SEQ ID NO: 44)
UCGGAUCCGUCUGAGCUUGGC, mmu-miR-100,
(SEQ ID NO: 45)
AACCCGUAGAUCCGAACUUGUG, mmu-miR-199a,
(SEQ ED NO: 46)
CCCAGUGUUCAGACU ACCUGUUC, mmu-miR-199b,
(SEQ ED NO: 47)
CCCAGUGUUU AGACU ACCUGUUC, mmu-miR-125a,
(SEQ ED NO: 48)
UCCCUGAGACCCUUUAACCUGUG, mmu-miR-22,
(SEQ ID NO: 49)
AAGCUGCCAGUUGAAGAACUGU, mmu-miR-434-3p,
(SEQ ID NO: 50)
UUUGAACCAUCACUCGACUCC, mmu-miR-34a,
(SEQ ID NO: 51)
UGGCAGUGUCUUAGCUGGUUGUU, mmu-miR-181c,
(SEQ ID NO: 52)
AACAUUCAACCUGUCGGUGAGU, mmu-miR-139,
(SEQ ID NO: 53)
UCUACAGUGCACGUGUCU, mmu-miR-130a,
(SEQ ID NO: 54)
CAGUGCAAUGUUAAAAGGGCAU, mmu-miR-322,
(SEQ ID NO: 55)
CAGCAGCAAUUCAUGUUUUGGA, mmu-miR-181a,
(SEQ ID NO: 56)
AACAUUCAACGCUGUCGGUGAGU, mmu-miR-125a,
(SEQ ID NO: 57)
UCCCUGAGACCCUUUAACCUGUG, mmu-miR-200b,
(SEQ ID NO: 58)
UAAUACUGCCUGGUAAUGAUGAC, mmu-miR-145,
(SEQ ID NO: 59)
GUCCAGUUUUCCCAGGAAUCCCUU, mmu-miR-127,
(SEQ ID NO: 60)
UCGGAUCCGUCUGAGCUUGGC, mmu-miR-199a,
(SEQ ID NO: 61)
CCCAGUGUUCAGACUACCUGUUC, mmu-miR-425,
(SEQ ID NO: 62)
AUCGGGAAUGUCGUGUCCGCC, mmu-miR-99b,
(SEQ ID NO: 63)
CACCCGU AGAACCGACCUUGCG, mmu-let-7e,
(SEQ ID NO: 64)
UGAGGUAGGAGGUUGUAUAGU, mmu-miR-195,
(SEQ ID NO: 65)
UAGCAGCACAGAAAUAUUGGC, mmu-miR-152,
(SEQ ID NO: 66)
UCAGUGCAUGACAGAACUUGGG, mmu-miR-125b,
(SEQ ID NO: 67)
UCCCUGAGACCCUAACUUGUGA, mmu-miR-187,
(SEQ ID NO: 68)
UCGUGUCUUGUGUUGCAGCCGG, mmu-miR-324-3p,
(SEQ ID NO: 69)
CCACUGCCCCAGGUGCUGCUGG, mmu-miR-150,
(SEQ ID NO: 70)
UCUCCCAACCCUUGUACCAGUG, mmu-miR-28,
(SEQ ID NO: 71)
AAGGAGCUCACAGUCUAUUGAG,
and mmu-miR-143
(SEQ ID NO: 72)
UGAGAUGAAGCACUGUAGCUCA, in a biological sample from the subject, and (ii) calculating altered expression of the at least 20 miRNAs relative to a reference, thereby identifying a subject as having, or having a propensity to develop, organ rejection.

2. The method of claim 1, wherein at least one miRNA from the at least 20 miRNAs is selected from the group consisting of: miR-182, miR-467, miR-434-3p, miR-181a, miR-19a, and miR-375, wherein an increase in the level of miR-467 or miR-19a or wherein a decrease in the level of miR-375, miR-182, miR-434-3p, or miR-181a indicates an increased likelihood of organ rejection.

3. The method of claim 1, wherein the transplanted organ is selected from the group consisting of: heart, kidney, liver, lung, and pancreas.

4. The method of claim 3, wherein the transplanted organ is kidney.

5. The method of claim 1, wherein expression of at least one miRNA from the at least 20 miRNAs is increased relative to the reference.

6. The method of claim 1, wherein expression of at least one miRNA from the at least 20 miRNAs is decreased relative to the reference.

7. The method of claim 1, wherein the amount of expression is determined using a microarray.

8. The method of claim 7, wherein the microarray comprises any member from the group consisting of a: chip, plate, bead, and membrane.

9. The method of claim 1, wherein the biological sample is selected from the group consisting of: blood cells, biopsy specimens, urine cells/urine sediment, and cells found in sputum.

10. A method for hybridizing one or more microRNAs in a sample, the method comprising:

(i) amplifying at least one miRNA obtained from a biological sample and selected from the group consisting of:

mmu-miR-134,
(SEQ ID NO: 1)
UGUGACUGGUUGACCAGAGGGG, mmu-miR-144,
(SEQ ID NO: 2)
UACAGUAUAGAUGAUGUACUAG, mmu-miR-466,
(SEQ ID NO: 3)
AUACAUACACGCACACAUAAGAC, mmu-miR-7,
(SEQ ID NO: 4)
UGGAAGACUAGUGAUUUUGUUG, mmu-miR-346,
(SEQ ID NO: 5)
UGUCUGCCCGAGUGCCUGCCUCU, mmu-miR-468,
(SEQ ID NO: 6)
UAUGACUGAUGUGCGUGUGUCU, mmu-miR-188,
(SEQ ID NO: 7)
CAUCCCUUGCAUGGUGGAGGGU, mmu-miR-298,
(SEQ ID NO: 8)
GGCAGAGGAGGGCUGUUCUUCC, mmu-miR-467,
(SEQ ID NO: 9)
AUAUACAUACACACACCUACAC, mmu-miR-292-5p,
(SEQ ID NO: 10)
ACUCAAACUGGGGGCUCUUUUG, mmu-miR-186,
(SEQ ID NO: 11)
CAAAGAAUUCUCCUUUUGGGCUU, mmu-miR-486,
(SEQ ID NO: 12)
UCCUGUACUGAGCUGCCCCGAG, mmu-miR-451,
(SEQ ID NO: 13)
AAACCGUUACCAUUACUGAGUU, mmu-miR-18,
(SEQ ID NO: 14)
UAAGGUGCAUCUAGUGCAGAUA, mmu-miR-25,
(SEQ ID NO: 15)
CAUUGCACUUGUCUCGGUCUGA, mmu-miR-223
(SEQ ID NO: 16)
UGUCAGUUUGUCAAAUACCCC, mmu-miR-320,
(SEQ ID NO: 17)
AAAAGCUGGGUUGAGAGGGCGAA, mmu-miR-148b,
(SEQ ID NO: 18)
UCAGUGCAUCACAGAACUUUGU, mmu-miR-21,
(SEQ ID NO: 19)
UAGCUUAUCAGACUGAUGUUGA, mmu-miR-124a,
(SEQ ID NO: 20)
UAAGGCACGCGGUGAAUGCC, -continued mmu-miR-19a,
(SEQ ID NO: 21)
UGUGCAAAUCUAUGCAAAACUGA, mmu-miR-301
(SEQ ID NO: 22)
CAGUGCAAUAGUAUUGUCAAAGC, mmu-miR-31,
(SEQ ID NO: 23)
AGGCAAGAUGCUGGCAUAGCUG, mmu-miR-20,
(SEQ ID NO: 24)
UAAAGUGCUUAUAGUGCAGGUAG, mmu-miR-29c,
(SEQ ID NO: 25)
UAGCACCAUUUGAAAUCGGU, mmu-miR-148a,
(SEQ ID NO: 26)
UCAGUGCACUACAGAACUUUGU, mmu-miR-17-5p,
(SEQ ID NO: 27)
CAAAGUGCUUACAGUGCAGGUAGU, mmu-miR-185,
(SEQ ID NO: 28)
UGGAGAGAAAGGCAGUUC, mmu-miR-106a,
(SEQ ID NO: 29)
CAAAGUGCUAACAGUGCAGGUA, mmu-miR-106b,
(SEQ ID NO: 30)
UAAAGUGCUGACAGUGCAGAU, mmu-miR-375,
(SEQ ID NO: 31)
UUUGUUCGUUCGGCUCGCGUGA, mmu-miR-216,
(SEQ ID NO: 32)
UAAUCUCAGCUGGCAACUGUG, mmu-miR-217,
(SEQ ID NO: 33)
UACUGCAUCAGGAACUGACUGGAU, mmu-miR-200a,
(SEQ ID NO: 34)
UAACACUGUCUGGUAACGAUGU, mmu-miR-200b,
(SEQ ID NO: 35)
UAAUACUGCCUGGUAAUGAUGAC, mmu-miR-429,
(SEQ ID NO: 36)
UAAUACUGUCUGGUAAUGCCGU, mmu-miR-200c,
(SEQ ID NO: 37)
UAAUACUGCCGGGUAAUGAUGG, mmu-miR-141
(SEQ ID NO: 38)
UAACACUGUCUGGUAAAGAUGG, mmu-miR-148a,
(SEQ ID NO: 39)
UCAGUGCACUACAGAACUUUGU, mmu-miR-152,
(SEQ ID NO: 40)
UCAGUGCAUGACAGAACUUGGG, mmu-miR-182,
UUUGGCAAUGGUAGAACUCACA, (SEQ ID NO: 41)

mmu-miR-99a,
ACCCGUAGAUCCGAUCUUGU, (SEQ ID NO: 42)

mmu-miR-130a,
CAGUGC AAUGUU AAAAGGGC AU, (SEQ ID NO: 43)

mmu-miR-127,
UCGGAUCCGUCUGAGCUUGGC, (SEQ ID NO: 44)

mmu-miR-100,
AACCCGUAGAUCCGAACUUGUG, (SEQ ID NO: 45)

mmu-miR-199a,
CCCAGUGUUCAGACU ACCGUUC, (SEQ ID NO: 46)

mmu-miR-199b,
CCCAGUGUUU AGACU ACCUGUUC, (SEQ ID NO: 47)

mmu-miR-125a,
UCCCUGAGACCCUUUAACCUGUG, (SEQ ID NO: 48)

mmu-miR-22,
AAGCUGCCAGUUGAAGAACUGU, (SEQ ID NO: 49)

mmu-miR-434-3p,
UUUGAACCAUCACUCGACUCC, (SEQ ID NO: 50)

mmu-miR-34a,
UGGCAGUGUCUUAGCUGGUUGUU, (SEQ ID NO: 51)

mmu-miR-181c,
AACAUUCAACCUGUCGGUGAGU, (SEQ ID NO: 52)

mmu-miR-139,
UCUACAGUGCACGUGUCU, (SEQ ID NO: 53)

mmu-miR-130a,
CAGUGCAAUGUUAAAAGGGCAU, (SEQ ID NO: 54)

mmu-miR-322,
CAGCAGCAAUUCAUGUUUUGGA, (SEQ ID NO: 55)

mmu-miR-181a,
AACAUUCAACGCUGUCGGUGAGU, (SEQ ID NO: 56)

mmu-miR-125a,
UCCCUGAGACCCUUUAACCUGUG, (SEQ ID NO: 57)

mmu-miR-200b,
UAAUACUGCCUGGUAAUGAUGAC, (SEQ ID NO: 58)

mmu-miR-145,
GUCCAGUUUUCCCAGGAAUCCCUU, (SEQ ID NO: 59)

mmu-miR-127,
UCGGAUCCGUCUGAGCUUGGC, (SEQ ID NO: 60)

mmu-miR-199a,
CCCAGUGUUCAGACUACCUGUUC, (SEQ ID NO: 61)

mmu-miR-425,
AUCGGGAAUGUCGUGUCCGCC, (SEQ ID NO: 62)

mmu-miR-99b,
CACCCGU AGAACCGACCUUGCG, (SEQ ID NO: 63)

mmu-let-7e,
UGAGGUAGGAGGUUGUAUAGU, (SEQ ID NO: 64)

mmu-miR-195,
UAGCAGCACAGAAAUAUUGGC, (SEQ ID NO: 65)

mmu-miR-152,
UCAGUGCAUGACAGAACUUGGG, (SEQ ID NO: 66)

mmu-miR-125b,
UCCCUGAGACCCUAACUUGUGA, (SEQ ID NO: 67)

mmu-miR-187,
UCGUGUCUUGUGUUGCAGCCGG, (SEQ ID NO: 68)

mmu-miR-324-3p,
CCACUGCCCCAGGUGCUGCUGG, (SEQ ID NO: 69)

mmu-miR-150,
UCUCCCAACCCUUGUACCAGUG, (SEQ ID NO: 70)

mmu-miR-28,
AAGGAGCUCACAGUCUAUUGAG, (SEQ ID NO: 71)
and mmu-miR-143
UGAGAUGAAGCACUGUAGCUCA, (SEQ ID NO: 72)

in the presence of one or more fluorescent nucleotides to generate one or more labeled cDNAs, wherein the biological sample is obtained from a subject having a transplanted organ, (ii) contacting the one or more labeled cDNAs with one or more complementary oligonucleotides bound to a microarray, and (ii) detecting conformational changes in the cDNA by detecting the presence of at least one hybridization product, wherein the at least one hybridization product is detected using a signal from the fluorescent nucleotides.

11. The method of claim 10, wherein at least 20 miRNAs are amplified to produce at least 20 labeled miRNAs.

12. The method of claim 1, wherein the at least 20 miRNAs consist essentially of miR-375, miR-216, miR-217, miR-200a, miR-200b, miR-429, miR-200c, miR-141, miR-134, miR-148a, miR-144, miR-466, miR-7, miR-346, miR-468, miR-188, miR-152, miR-298, miR-182, and miR-99a.

* * * * *

SEQUENCE LISTING

```
<160> NUMBER OF SEQ ID NOS: 84

<210> SEQ ID NO 1
<211> LENGTH: 22
<212> TYPE: RNA
<213> ORGANISM: Mus musculus

<400> SEQUENCE: 1
ugugacuggu ugaccagagg gg                                              22
```

```
<210> SEQ ID NO 2
<211> LENGTH: 22
<212> TYPE: RNA
<213> ORGANISM: Mus musculus

<400> SEQUENCE: 2
uacaguauag augauguacu ag                                              22

<210> SEQ ID NO 3
<211> LENGTH: 23
<212> TYPE: RNA
<213> ORGANISM: Mus musculus

<400> SEQUENCE: 3
auacauacac gcacacauaa gac                                             23

<210> SEQ ID NO 4
<211> LENGTH: 22
<212> TYPE: RNA
<213> ORGANISM: Mus musculus

<400> SEQUENCE: 4
uggaagacua gugauuuugu ug                                              22

<210> SEQ ID NO 5
<211> LENGTH: 23
<212> TYPE: RNA
<213> ORGANISM: Mus musculus

<400> SEQUENCE: 5
ugucugcccg agugccugcc ucu                                             23

<210> SEQ ID NO 6
<211> LENGTH: 22
<212> TYPE: RNA
<213> ORGANISM: Mus musculus

<400> SEQUENCE: 6
uaugacugau gugcgugugu cu                                              22

<210> SEQ ID NO 7
<211> LENGTH: 22
<212> TYPE: RNA
<213> ORGANISM: Mus musculus

<400> SEQUENCE: 7
caucccuugc augguggagg gu                                              22

<210> SEQ ID NO 8
<211> LENGTH: 22
<212> TYPE: RNA
<213> ORGANISM: Mus musculus

<400> SEQUENCE: 8
ggcagaggag ggcuguucuu cc                                              22

<210> SEQ ID NO 9
<211> LENGTH: 22
<212> TYPE: RNA
<213> ORGANISM: Mus musculus

<400> SEQUENCE: 9
auauacauac acacaccuac ac                                              22
```

```
<210> SEQ ID NO 10
<211> LENGTH: 22
<212> TYPE: RNA
<213> ORGANISM: Mus musculus

<400> SEQUENCE: 10
acucaaacug ggggcucuuu ug                                              22

<210> SEQ ID NO 11
<211> LENGTH: 23
<212> TYPE: RNA
<213> ORGANISM: Mus musculus

<400> SEQUENCE: 11
caaagaauuc uccuuuuggg cuu                                             23

<210> SEQ ID NO 12
<211> LENGTH: 22
<212> TYPE: RNA
<213> ORGANISM: Mus musculus

<400> SEQUENCE: 12
uccuguacug agcugccccg ag                                              22

<210> SEQ ID NO 13
<211> LENGTH: 22
<212> TYPE: RNA
<213> ORGANISM: Mus musculus

<400> SEQUENCE: 13
aaaccguuac cauuacugag uu                                              22

<210> SEQ ID NO 14
<211> LENGTH: 22
<212> TYPE: RNA
<213> ORGANISM: Mus musculus

<400> SEQUENCE: 14
uaaggugcau cuagugcaga ua                                              22

<210> SEQ ID NO 15
<211> LENGTH: 22
<212> TYPE: RNA
<213> ORGANISM: Mus musculus

<400> SEQUENCE: 15
cauugcacuu gucucggucu ga                                              22

<210> SEQ ID NO 16
<211> LENGTH: 21
<212> TYPE: RNA
<213> ORGANISM: Mus musculus

<400> SEQUENCE: 16
ugucaguuug ucaaauaccc c                                               21

<210> SEQ ID NO 17
<211> LENGTH: 23
<212> TYPE: RNA
<213> ORGANISM: Mus musculus

<400> SEQUENCE: 17
aaaagcuggg uugagagggc gaa                                             23
```

```
<210> SEQ ID NO 18
<211> LENGTH: 22
<212> TYPE: RNA
<213> ORGANISM: Mus musculus

<400> SEQUENCE: 18
ucagugcauc acagaacuuu gu                                              22

<210> SEQ ID NO 19
<211> LENGTH: 22
<212> TYPE: RNA
<213> ORGANISM: Mus musculus

<400> SEQUENCE: 19
uagcuuauca gacugauguu ga                                              22

<210> SEQ ID NO 20
<211> LENGTH: 20
<212> TYPE: RNA
<213> ORGANISM: Mus musculus

<400> SEQUENCE: 20
uaaggcacgc ggugaaugcc                                                 20

<210> SEQ ID NO 21
<211> LENGTH: 23
<212> TYPE: RNA
<213> ORGANISM: Mus musculus

<400> SEQUENCE: 21
ugugcaaauc uaugcaaaac uga                                             23

<210> SEQ ID NO 22
<211> LENGTH: 23
<212> TYPE: RNA
<213> ORGANISM: Mus musculus

<400> SEQUENCE: 22
cagugcaaua guauugucaa agc                                             23

<210> SEQ ID NO 23
<211> LENGTH: 22
<212> TYPE: RNA
<213> ORGANISM: Mus musculus

<400> SEQUENCE: 23
aggcaagaug cuggcauagc ug                                              22

<210> SEQ ID NO 24
<211> LENGTH: 23
<212> TYPE: RNA
<213> ORGANISM: Mus musculus

<400> SEQUENCE: 24
uaaagugcuu auagugcagg uag                                             23

<210> SEQ ID NO 25
<211> LENGTH: 20
<212> TYPE: RNA
<213> ORGANISM: Mus musculus

<400> SEQUENCE: 25
```
uagcaccauu ugaaaucggu                                                    20

<210> SEQ ID NO 26
<211> LENGTH: 22
<212> TYPE: RNA
<213> ORGANISM: Mus musculus

<400> SEQUENCE: 26
ucagugcacu acagaacuuu gu                                                 22

<210> SEQ ID NO 27
<211> LENGTH: 24
<212> TYPE: RNA
<213> ORGANISM: Mus musculus

<400> SEQUENCE: 27
caaagugcuu acagugcagg uagu                                               24

<210> SEQ ID NO 28
<211> LENGTH: 18
<212> TYPE: RNA
<213> ORGANISM: Mus musculus

<400> SEQUENCE: 28
uggagagaaa ggcaguuc                                                      18

<210> SEQ ID NO 29
<211> LENGTH: 22
<212> TYPE: RNA
<213> ORGANISM: Mus musculus

<400> SEQUENCE: 29
caaagugcua acagugcagg ua                                                 22

<210> SEQ ID NO 30
<211> LENGTH: 21
<212> TYPE: RNA
<213> ORGANISM: Mus musculus

<400> SEQUENCE: 30
uaaagugcug acagugcaga u                                                  21

<210> SEQ ID NO 31
<211> LENGTH: 22
<212> TYPE: RNA
<213> ORGANISM: Mus musculus

<400> SEQUENCE: 31
uuuguucguu cggcucgcgu ga                                                 22

<210> SEQ ID NO 32
<211> LENGTH: 21
<212> TYPE: RNA
<213> ORGANISM: Mus musculus

<400> SEQUENCE: 32
uaaucucagc uggcaacugu g                                                  21

<210> SEQ ID NO 33
<211> LENGTH: 24
<212> TYPE: RNA
<213> ORGANISM: Mus musculus

<400> SEQUENCE: 33

-continued

| | |
|---|---|
| uacugcauca ggaacugacu ggau | 24 |

<210> SEQ ID NO 34
<211> LENGTH: 22
<212> TYPE: RNA
<213> ORGANISM: Mus musculus

<400> SEQUENCE: 34

| | |
|---|---|
| uaacacuguc ugguaacgau gu | 22 |

<210> SEQ ID NO 35
<211> LENGTH: 23
<212> TYPE: RNA
<213> ORGANISM: Mus musculus

<400> SEQUENCE: 35

| | |
|---|---|
| uaauacugcc ugguaaugau gac | 23 |

<210> SEQ ID NO 36
<211> LENGTH: 22
<212> TYPE: RNA
<213> ORGANISM: Mus musculus

<400> SEQUENCE: 36

| | |
|---|---|
| uaauacuguc ugguaaugcc gu | 22 |

<210> SEQ ID NO 37
<211> LENGTH: 22
<212> TYPE: RNA
<213> ORGANISM: Mus musculus

<400> SEQUENCE: 37

| | |
|---|---|
| uaauacugcc ggguaaugau gg | 22 |

<210> SEQ ID NO 38
<211> LENGTH: 22
<212> TYPE: RNA
<213> ORGANISM: Mus musculus

<400> SEQUENCE: 38

| | |
|---|---|
| uaacacuguc ugguaaagau gg | 22 |

<210> SEQ ID NO 39
<211> LENGTH: 22
<212> TYPE: RNA
<213> ORGANISM: Mus musculus

<400> SEQUENCE: 39

| | |
|---|---|
| ucagugcacu acagaacuuu gu | 22 |

<210> SEQ ID NO 40
<211> LENGTH: 22
<212> TYPE: RNA
<213> ORGANISM: Mus musculus

<400> SEQUENCE: 40

| | |
|---|---|
| ucagugcaug acagaacuug gg | 22 |

<210> SEQ ID NO 41
<211> LENGTH: 22
<212> TYPE: RNA
<213> ORGANISM: Mus musculus

```
<400> SEQUENCE: 41
uuuggcaaug guagaacuca ca                                          22

<210> SEQ ID NO 42
<211> LENGTH: 20
<212> TYPE: RNA
<213> ORGANISM: Mus musculus

<400> SEQUENCE: 42
acccguagau ccgaucuugu                                             20

<210> SEQ ID NO 43
<211> LENGTH: 22
<212> TYPE: RNA
<213> ORGANISM: Mus musculus

<400> SEQUENCE: 43
cagugcaaug uuaaaagggc au                                          22

<210> SEQ ID NO 44
<211> LENGTH: 21
<212> TYPE: RNA
<213> ORGANISM: Mus musculus

<400> SEQUENCE: 44
ucggauccgu cugagcuugg c                                           21

<210> SEQ ID NO 45
<211> LENGTH: 22
<212> TYPE: RNA
<213> ORGANISM: Mus musculus

<400> SEQUENCE: 45
aacccguaga uccgaacuug ug                                          22

<210> SEQ ID NO 46
<211> LENGTH: 23
<212> TYPE: RNA
<213> ORGANISM: Mus musculus

<400> SEQUENCE: 46
cccaguguuc agacuaccug uuc                                         23

<210> SEQ ID NO 47
<211> LENGTH: 23
<212> TYPE: RNA
<213> ORGANISM: Mus musculus

<400> SEQUENCE: 47
cccaguguuu agacuaccug uuc                                         23

<210> SEQ ID NO 48
<211> LENGTH: 23
<212> TYPE: RNA
<213> ORGANISM: Mus musculus

<400> SEQUENCE: 48
ucccugagac ccuuuaaccu gug                                         23

<210> SEQ ID NO 49
<211> LENGTH: 22
<212> TYPE: RNA
<213> ORGANISM: Mus musculus
```

<400> SEQUENCE: 49
aagcugccag uugaagaacu gu                                           22

<210> SEQ ID NO 50
<211> LENGTH: 21
<212> TYPE: RNA
<213> ORGANISM: Mus musculus

<400> SEQUENCE: 50
uuugaaccau cacucgacuc c                                            21

<210> SEQ ID NO 51
<211> LENGTH: 23
<212> TYPE: RNA
<213> ORGANISM: Mus musculus

<400> SEQUENCE: 51
uggcaguguc uuagcugguu guu                                          23

<210> SEQ ID NO 52
<211> LENGTH: 22
<212> TYPE: RNA
<213> ORGANISM: Mus musculus

<400> SEQUENCE: 52
aacauucaac cugucgguga gu                                           22

<210> SEQ ID NO 53
<211> LENGTH: 18
<212> TYPE: RNA
<213> ORGANISM: Mus musculus

<400> SEQUENCE: 53
ucuacagugc acgugucu                                                18

<210> SEQ ID NO 54
<211> LENGTH: 22
<212> TYPE: RNA
<213> ORGANISM: Mus musculus

<400> SEQUENCE: 54
cagugcaaug uuaaaagggc au                                           22

<210> SEQ ID NO 55
<211> LENGTH: 22
<212> TYPE: RNA
<213> ORGANISM: Mus musculus

<400> SEQUENCE: 55
cagcagcaau ucauguuuug ga                                           22

<210> SEQ ID NO 56
<211> LENGTH: 23
<212> TYPE: RNA
<213> ORGANISM: Mus musculus

<400> SEQUENCE: 56
aacauucaac gcugucggug agu                                          23

<210> SEQ ID NO 57
<211> LENGTH: 23
<212> TYPE: RNA

```
<213> ORGANISM: Mus musculus

<400> SEQUENCE: 57
ucccugagac ccuuuaaccu gug                                              23

<210> SEQ ID NO 58
<211> LENGTH: 23
<212> TYPE: RNA
<213> ORGANISM: Mus musculus

<400> SEQUENCE: 58
uaauacugcc ugguaaugau gac                                              23

<210> SEQ ID NO 59
<211> LENGTH: 24
<212> TYPE: RNA
<213> ORGANISM: Mus musculus

<400> SEQUENCE: 59
guccaguuuu cccaggaauc ccuu                                             24

<210> SEQ ID NO 60
<211> LENGTH: 21
<212> TYPE: RNA
<213> ORGANISM: Mus musculus

<400> SEQUENCE: 60
ucggauccgu cugagcuugg c                                                21

<210> SEQ ID NO 61
<211> LENGTH: 23
<212> TYPE: RNA
<213> ORGANISM: Mus musculus

<400> SEQUENCE: 61
cccaguguuc agacuaccug uuc                                              23

<210> SEQ ID NO 62
<211> LENGTH: 21
<212> TYPE: RNA
<213> ORGANISM: Mus musculus

<400> SEQUENCE: 62
aucgggaaug ucguguccgc c                                                21

<210> SEQ ID NO 63
<211> LENGTH: 22
<212> TYPE: RNA
<213> ORGANISM: Mus musculus

<400> SEQUENCE: 63
cacccguaga accgaccuug cg                                               22

<210> SEQ ID NO 64
<211> LENGTH: 21
<212> TYPE: RNA
<213> ORGANISM: Mus musculus

<400> SEQUENCE: 64
ugagguagga gguuguauag u                                                21

<210> SEQ ID NO 65
<211> LENGTH: 21
```

```
<212> TYPE: RNA
<213> ORGANISM: Mus musculus

<400> SEQUENCE: 65
uagcagcaca gaaauauugg c                                         21

<210> SEQ ID NO 66
<211> LENGTH: 22
<212> TYPE: RNA
<213> ORGANISM: Mus musculus

<400> SEQUENCE: 66
ucagugcaug acagaacuug gg                                        22

<210> SEQ ID NO 67
<211> LENGTH: 22
<212> TYPE: RNA
<213> ORGANISM: Mus musculus

<400> SEQUENCE: 67
ucccugagac ccuaacuugu ga                                        22

<210> SEQ ID NO 68
<211> LENGTH: 22
<212> TYPE: RNA
<213> ORGANISM: Mus musculus

<400> SEQUENCE: 68
ucgugucuug uguugcagcc gg                                        22

<210> SEQ ID NO 69
<211> LENGTH: 22
<212> TYPE: RNA
<213> ORGANISM: Mus musculus

<400> SEQUENCE: 69
ccacugcccc aggugcugcu gg                                        22

<210> SEQ ID NO 70
<211> LENGTH: 22
<212> TYPE: RNA
<213> ORGANISM: Mus musculus

<400> SEQUENCE: 70
ucucccaacc cuuguaccag ug                                        22

<210> SEQ ID NO 71
<211> LENGTH: 22
<212> TYPE: RNA
<213> ORGANISM: Mus musculus

<400> SEQUENCE: 71
aaggagcuca cagucuauug ag                                        22

<210> SEQ ID NO 72
<211> LENGTH: 22
<212> TYPE: RNA
<213> ORGANISM: Mus musculus

<400> SEQUENCE: 72
ugagaugaag cacuguagcu ca                                        22

<210> SEQ ID NO 73
```

```
<211> LENGTH: 71
<212> TYPE: RNA
<213> ORGANISM: Mus musculus

<400> SEQUENCE: 73
agggugugug acugguugac cagaggggcg ugcacucugu ucacccugug ggccaccuag     60
ucaccaaccc u                                                          71

<210> SEQ ID NO 74
<211> LENGTH: 73
<212> TYPE: RNA
<213> ORGANISM: Homo sapiens

<400> SEQUENCE: 74
cagggugugu gacugguuga ccagaggggc augcacugug uucacccugu gggccaccua     60
gucaccaacc cuc                                                        73

<210> SEQ ID NO 75
<211> LENGTH: 71
<212> TYPE: DNA
<213> ORGANISM: Mus musculus

<400> SEQUENCE: 75
agggtgtgtg actggttgac cagaggggcg tgcactctgt tcaccctgtg ggccacctag     60
tcaccaaccc t                                                          71

<210> SEQ ID NO 76
<211> LENGTH: 71
<212> TYPE: DNA
<213> ORGANISM: Homo sapiens

<400> SEQUENCE: 76
agggtgtgtg actggttgac cagaggggca tgcactgtgt tcaccctgtg ggccacctag     60
tcaccaaccc t                                                          71

<210> SEQ ID NO 77
<211> LENGTH: 66
<212> TYPE: RNA
<213> ORGANISM: Mus musculus

<400> SEQUENCE: 77
ggcugggaua ucaucauaua cuguaaguuu gugaugagac acuacaguau agaugaugua     60
cuaguc                                                                66

<210> SEQ ID NO 78
<211> LENGTH: 86
<212> TYPE: RNA
<213> ORGANISM: Homo sapiens

<400> SEQUENCE: 78
uggggcccug gcugggauau caucauauac uguaaguuug cgaugagaca cuacaguaua     60
gaugauguac uaguccgggc accccc                                          86

<210> SEQ ID NO 79
<211> LENGTH: 66
<212> TYPE: DNA
<213> ORGANISM: Mus musculus

<400> SEQUENCE: 79
ggctgggata tcatcatata ctgtaagttt gtgatgagac actacagtat agatgatgta     60
```

-continued

```
ctagtc                                                              66

<210> SEQ ID NO 80
<211> LENGTH: 66
<212> TYPE: DNA
<213> ORGANISM: Homo sapiens

<400> SEQUENCE: 80
ggctgggata tcatcatata ctgtaagttt gcgatgagac actacagtat agatgatgta   60
ctagtc                                                              66

<210> SEQ ID NO 81
<211> LENGTH: 68
<212> TYPE: RNA
<213> ORGANISM: Mus musculus

<400> SEQUENCE: 81
ucucacaucc cuugcauggu ggagggugag cucucugaaa accccuccca caugcagggu   60
uugcagga                                                            68

<210> SEQ ID NO 82
<211> LENGTH: 86
<212> TYPE: RNA
<213> ORGANISM: Homo sapiens

<400> SEQUENCE: 82
ugcucccucu cucacauccc uugcauggug gagggugagc uuucugaaaa ccccucccac   60
augcaggguu ugcaggaugg cgagcc                                        86

<210> SEQ ID NO 83
<211> LENGTH: 68
<212> TYPE: DNA
<213> ORGANISM: Mus musculus

<400> SEQUENCE: 83
tctcacatcc cttgcatggt ggagggtgag ctctctgaaa accctccca catgcagggt    60 ttgcagga                                                            68

<210> SEQ ID NO 84
<211> LENGTH: 68
<212> TYPE: DNA
<213> ORGANISM: Homo sapiens

<400> SEQUENCE: 84
tctcacatcc cttgcatggt ggagggtgag ctttctgaaa accctccca catgcagggt    60 ttgcagga                                                            68
```